US012746249B2

(12) United States Patent
Jennewein et al.

(10) Patent No.: US 12,746,249 B2
(45) Date of Patent: Sep. 29, 2026

(54) METHOD FOR DRYING HUMAN MILK OLIGOSACCHARIDES

(71) Applicant: Chr. Hansen A/S, Hoersholm (DK)

(72) Inventors: Stefan Jennewein, Bad Honnef (DE); Mischa Baier, Düsseldorf (DE); Tobias Seitz, Bonn (DE); Markus Helfrich, Bad Hönningeh (DE)

(73) Assignee: Chr. Hansen A/S, Hoersholm (DK)

( * ) Notice: Subject to any disclaimer, the term of this patent is extended or adjusted under 35 U.S.C. 154(b) by 924 days.

(21) Appl. No.: 17/776,699

(22) PCT Filed: Nov. 12, 2020

(86) PCT No.: PCT/EP2020/081920
§ 371 (c)(1),
(2) Date: May 13, 2022

(87) PCT Pub. No.: WO2021/094459
PCT Pub. Date: May 20, 2021

(65) Prior Publication Data
US 2022/0395519 A1 Dec. 15, 2022

(30) Foreign Application Priority Data
Nov. 15, 2019 (EP) .................................... 19209604

(51) Int. Cl.

| | |
|---|---|
| ***A61K 31/702*** | (2006.01) |
| ***A23L 2/39*** | (2006.01) |
| ***A23L 33/125*** | (2016.01) |
| ***A23P 10/20*** | (2016.01) |
| ***A23P 10/40*** | (2016.01) |

(52) U.S. Cl.
CPC .............. *A61K 31/702* (2013.01); *A23L 2/39* (2013.01); *A23L 33/125* (2016.08); *A23P 10/20* (2016.08); *A23P 10/40* (2016.08)

(58) Field of Classification Search
CPC ................................ A23B 2/90; A61K 31/702
See application file for complete search history.

(56) References Cited

FOREIGN PATENT DOCUMENTS

| | | | | |
|---|---|---|---|---|
| CN | 110122865 A | 8/2019 | | |
| EP | 2885977 A1 * | 6/2015 | .......... | A23C 9/1425 |
| JP | H10179041 A | 7/1998 | | |
| JP | 2001208476 A | 8/2001 | | |
| JP | 2009065937 A | 4/2009 | | |
| JP | 2011239731 A | 12/2011 | | |
| RU | 2422045 C2 | 6/2011 | | |
| RU | 2442438 C2 | 2/2012 | | |
| WO | 2006087391 A1 | 8/2006 | | |
| WO | 2006112718 A2 | 10/2006 | | |
| WO | 2018013402 A1 | 1/2018 | | |
| WO | WO-2019063757 A1 * | 4/2019 | ............... | C07H 1/08 |
| WO | 2019101629 A1 | 5/2019 | | |
| WO | 2019110800 A1 | 6/2019 | | |

OTHER PUBLICATIONS

Priem, Glycobiology vol. 12 No. 4 pp. 235-240, 2002. (Year: 2002).*
Cammerer et al., "Nonenzymatic browning reactions of retro-aldol degradation products of carbohydrates," Eur Food Res Technol., 1999, 209:261-265.
Machine Translation of CN110122865, dated Aug. 16, 2019, 7 pages.
Machine Translation of JPH10179041, dated Jul. 7, 1998, 6 pages.
Martinez-Camacho et al., "Chitosan composite films: Thermal, structural, mechanical and antifungal properties," Carbohyd. Polym., 2010, 82(2):305-315.
Urashima et al., Milk Oligosaccharides, 2011, Nova Medical Books, New York, 54 pages.
Van Der Fels-Klerx et al., "Acrylamide and 5-hydroxymethylfurfural formation during baking of biscuits: NaCl and temperature-time profile effects and kinetics," Food Res. Int., 2014, 57:210-217.
Wilson et al., "Bio-Based Chemicals: carbohydrate conversion and utilisation," Advances in Biorefineries: Biomass and Waste Supply Chain Exploitation, 2014, Chapter 29, pp. 624-658.
Zeng Qingxiao, 2008, Basic Knowledge of Food Safety, p. 182.
Guan Zhengxue, 2000, Q&A on Development and Production Technology of Health Food, p. 185.
Zou Xiaobo, 2020, Food Processing Machinery and Equipment, p. 241.
Zhang Jiguang, 2004, Catalyst Preparation Process Technology, p. 179.
Chen Zhibin, 2012, Food Processing, p. 67.
Bechtold et al., "Potenzial von Prozessintegration mit Adsorbern zur Herstellung seltener Monosaccharide—eine modellba-sierte Untersuchung," Chemie Ingenieur Technik, 2010, 82:65-75.
Bhushani et al., "Freeze Drying," Handbook of Drying for Dairy Products, 2017, Chapter 6, 95-121.
Courtois et al., "Roller and drum drying for food powder production," Handbook of Food Powders, Processes and Properties, 2013, Chapter 4, 85-104.
Davidson et al., "A Model for Mechanical Degradation of Wheat Starch in a Single-Screw Extruder," J. Food Sci., 2006, 49(4):1154-1157.
Fagerson, "Thermal degradation of carbohydrates; a review," J. Agric. Food Chem., 1969, 17(4):747-750.
Ishwarya et al. "Spray Drying," Handbook of Drying for Dairy Products, John Wiley & Sons, 2017, Chapter 5, 57-94.
Ishwarya et al., "Spray freeze drying or freeze spary drying can also be uses as a drying process for carbohydrate-containing foods," Handbook of Drying for Dairy Products, 2017, Chapter 7, 123-148.
Karthik et al., "Drum Drying," Handbook of Drying for Dairy Products, 2017, Chapter 4, 43-56.

(Continued)

*Primary Examiner* — Layla D Berry
(74) *Attorney, Agent, or Firm* — Kelly Reynolds

(57) ABSTRACT

The present invention relates to a method for drying human milk oligosaccharides (HMOs). More specifically, the present invention is related to a method of roller drying or drum drying of human milk oligosaccharides in a simple and economical way.

16 Claims, 14 Drawing Sheets

(56) References Cited

OTHER PUBLICATIONS

Liu et al., "Mechanism of Degradation of Starch, a Highly Branched Polymer, during Extrusion," Macromolecules, 2010, 43(6):2855-2864.
Marx-Figini et al., "Studies on the mechanical degradation of cellulose," Macromol. Mater. Eng., 1995, 224(1):179-189.
Ott, "Mechanism of the mechanical degradation of cellulose," J. Polym. Sci. A. Pol. Chem., 1964, 2:973-982.
Ratti, "Freeze-drying is used to dry carbohydrates or carbohydrate-containing food," Freeze-Drying for Food Powder Production, 2013, Chapter 3, 57-84.
Woo et al., "Spray Drying for Food Powder Production," Handbook of Food Powders, Processes and Properties, 2013, Chapter 2, pp. 29-56.

* cited by examiner

METHOD FOR DRYING HUMAN MILK OLIGOSACCHARIDES

CROSS-REFERENCE TO RELATED APPLICATIONS

This application is a national stage application of International Patent Application No. PCT/EP2020/081920, filed Nov. 12, 2020, which claims priority to European Patent Application No. 19209604.8, filed Nov. 15, 2019, each of which is incorporated in their entirety by reference herein.

FIELD OF THE INVENTION

The present invention relates to a method for drying human milk oligosaccharides (HMOs). More specifically, the present invention is related to a method of roller drying or drum drying of human milk oligosaccharides.

BACKGROUND

Human milk is regarded as the best diet for the development of an infant. It is composed of fats, proteins, vitamins, minerals, trace elements and complex oligosaccharides. Besides lactose, human milk, as well as milk of other mammals, contains various structurally diverse oligosaccharides which are also known as human milk oligosaccharides (HMOs) (Usashima T. et al., 2011, Milk 20 Oligosaccharides, Nova Biomedical Books, New York ISBN 978-1-61122-831-1). Today it is thought that there are more than 150 structurally different oligosaccharides found in human milk. With very few exceptions, HMOs are characterized by a lactose disaccharide residue at their reducing ends on the one hand. On the other hand, many HMOs contain a fucose residue, a galactose residue, a N-acetylglucosamine or a N-acetylneuraminic acid residue at their non-reducing end. Furthermore, there are linear as well as branched representatives. Generally, the monosaccharide residues of HMOs are D-glucose, D-galactose, N-acetylglucosamine, L-fucose and N-acetylneuraminic acid (the latter also known as sialic acid or lactaminic acid). The importance of HMOs for infant nutrition is directly linked to their biological activities including protection of the neonate from pathogens, supporting development of the infant's immune system and cognitive abilities. In addition, HMOs serve as a substrate for beneficial bacteria like Bifidobacteria or Lactobacilli.

Due to the challenges involved in the chemical synthesis of human milk oligosaccharides, several enzymatic methods and fermentative approaches were developed. In particular, the fermentative approach requires purification of the desired oligosaccharide from a highly complex fermentation broth containing several hundreds of different individual compounds. The carbohydrate fraction of the fermentation broth alone is composed of a complex mixture of mono- and oligosaccharides as well as derivatives thereof including substrates (e.g. lactose, fructose, glucose, saccharose and other sugars used as carbon source), biosynthetic intermediates, individual monosaccharides (such as glucose, galactose, N-acetylglucosamine, L-fucose and N-acetylneuraminic acid), metabolic side products and other oligo- and polysaccharides synthesized by the microbe. Moreover, the structures of many of the oligosaccharides occurring in the fermentation broth are hard to identify (e.g. oligosaccharides produced by the synthesizing host naturally like cell surface glycosylation structures or oligosaccharides produced by the organism as a result of stress). Thus, in many cases the purification and formulation of a biotechnological product can be much more expensive and time-consuming than its production by fermentation.

In addition, the HMOs thus produced, not only need to be purified, but also isolated, and more ideally, dried. The drying process is in principle subject to special requirements. The saccharides to be isolated and dried generally show chemical reactivity comparable to standard primary or secondary alcohols, amides, α-functionalized carboxylic acids, acetals and hemi-acetals. Furthermore, these structures are redox- and also biologically active and in addition temperature-sensitive. Therefore, the drying process must be very gentle and must not stress the material in excess by, for example, mechanical stress, also the material must not be exposed to a high heat impact. Moreover, materials used in the drying-machinery must be inert to the carbohydrate and meet food quality criteria.

Specifically, the sugars to be processed within the present invention can be considered as macroscopic materials located at the interface between low molecular weight and high molecular weight materials, macromolecular or even oligomeric and/or polymeric materials. The substance classes mentioned above differ in many aspects, but in the present application, it is of crucial importance that oligomeric sugars such as HMOs, as well as polymeric sugars such as, for example, starch, cellulose or chitin, are not chemically damaged by mechanical stress (Liu, W.-C. et al., Macromolecules, 2010, 43(6), 2855-2864; Davidson, V. J. et al. J. Food Sci. 1984, 49(4), 1154-1157; Ott, R. L., J. Polym. Sci. A Pol. Chem. 1964, 2, 973-982; Marx-Figini, M., Macromol. Mater. Eng. 1995, 224, 1, 179-189; Martinez-Camacho, A. P., Carbohyd. Polym. 2010, 82, 2, 305-315). Furthermore, dissolved sugar entities are able to react chemically by oxidative or reductive conditions, which need the use of inert materials and conditions, and generally makes attractive that drying of such materials be made in a vacuum environment or under protective gas. Another aspect to be considered, which makes the treated sugar labile, is that it undergoes all kinds of intra- and intermolecular substitutions and hydrolysis reactions, which in extreme cases may even lead to disintegration and coloration of the end product, by for example, the formation of hydroxymethylfurfural (HMF), which is a well-known sugar decomposition product in literature, occurring when applying too basic, too acidic and/or too hot conditions. (Cammerer et al., Eur. Food Res. Technol. 1999, 209(3-4), 261-265; Fagerson, I. S., J. Agric. Food Chem. 1969, 17(4), 747-750; Wilson, K. et al., 2014, Chapter 19, Bio-based chemicals from biorefining: carbohydrate conversion and utilization, 624-658, In Waldron, K. (Editor), Advances in Biorefineries: Biomass and Waste Supply Chain Exploitation, ISBN: 978-0-85709-521-3; Van der Fels-Klerx, H. J. et al., Food Res. Int. 2014, 57, 210-217).

In principle, different drying methods can be considered in terms of how the material is or should be characterized before drying, how the drying process works and which properties of the material can be derived from the drying method.

The treated sugars may either be present already dissolved before drying or as a suspension or as an emulsion. If the sugar is dissolved, the material must be recovered from the solution in an amorphous or crystalline form, where the excess solvent must be removed by draining and/or drying. If, on the other hand, the sugar is present as a suspension, only excess solvent must be removed from the sugar mass. When a crystalline material is obtained, this will typically be formed in a specific hydrate form or even without any crystal water, this is the reason why there is certain water content in the dried material. Then, if the sugar is obtained amorphously, there cannot be any crystal water, but depending on the method of drying, a certain residual moisture is expected. The hydrate form and the residual water content influence the macroscopic properties of the material, such as, solubility and hygroscopicity. In addition to the residual moisture, each drying method is accompanied by a specific texture of the material and a particle size, which also influence the macroscopic properties of the material, such as, hygroscopicity and flowability.

Known processes for drying mono-, oligo- and polysaccharides as well as all other kinds of food products containing carbohydrates, non-food products containing carbohydrates and products that do not contain carbohydrates will be mentioned as follow.

Crystallization followed by the removal of the mother liqueur and followed by drying of the obtained crystals when dealing with pure fractions of mono- or oligosaccharides or a single form of mono- or oligosaccharide such as for example glucose, galactose, mannose, fructose, ribose, rhamnose, fucose, N-acetylneuraminic acid, sucrose, lactose, maltose as well as N-acetylated variants of the mentioned sugars or all kinds of oligomeric human milk oligosaccharides. Spray-drying is another drying process that is often used for drying and for the formulation of carbohydrates or carbohydrate-containing foods (Woo, M. W. et al. 2013, Chapter 2, Spray drying for food powder production, 29-56, In Bhandari, B., Bansal, N., Zhang, M., Schuck, P., (Editors) Handbook of Food Powders, Processes and Properties, ISBN: 978-0-85709-513-8; Ishwarya, S. P., Chapter 5: Spray Drying, 57-94, In Anandharamakrishnan, C. (Editor) Handbook of Drying for Dairy Products, ISBN: 9781118930526). Freeze-drying is used to dry carbohydrates or carbohydrate-containing food (Ratti, C. 2013, Chapter 3, Freeze drying for food powder production, 57-84, In Bhandari, B., Bansal, N., Zhang, M., Schuck, P., (Editors) Handbook of Food Powders, Processes and Properties, ISBN: 978-0-85709-513-8; Bhushani, A., Chapter 6: Freeze Drying, 95 121, In Anandharamakrishnan, C. (Editor) Handbook of Drying for Dairy Products, ISBN: 9781118930526). Spray freeze drying or freeze spray drying can also be used as a drying process for carbohydrate-containing foods (Ishwarya, S. P., Chapter 7: Spray Freeze Drying, 123-148, In Anandharamakrishnan, C. (Editor) Handbook of Drying for Dairy Products, ISBN: 9781118930526). Band and or belt drying as well as vacuum band or vacuum belt drying. And finally, roller drying, also known as drum drying or vacuum roller drying or vacuum drum drying (Courtois, F. 2013, Chapter 4, Roller and drum drying for food powder production, 85-104, In Bhandari, B., Bansal, N., Zhang, M., Schuck, P., (Editors) Handbook of Food Powders, Processes and Properties, ISBN: 978-0-85709-513-8; Karthik, P. et al., Chapter 4: Drum Drying, 43 56, In Anandharamakrishnan, C. (Editor) Handbook of Drying for Dairy Products, ISBN: 9781118930526). It is important to consider that, when a vacuum environment is applied to band or belt drying and roller or drum drying, it significantly changes the process as well as the product parameters, reason why, these methods should be considered individually.

Sugars cannot simply be dried from their solutions, but must undergo special drying procedures. The reason for this lies in the fact that sugars have water-resembling alcohol functionalities and generally are likely to interact with water. This is why sugar solubility is generally high in water and water-containing mixtures. When attempting to isolate carbohydrates from solutions by means of a simple drying, sugars tend to form gels or hydrogels, from which crystallization is hindered due to the reduced mobility of the sugar molecules and the limited degrees of freedom. However, thus virtually all homomeric sugars can be crystallized, the crystallization, draining and subsequent drying of the crystal mass, followed by washing and removal of non-crystallized sugar molecules as well as impurities, is a well-established method of sugar processing in the industry.

It should be considered, however, that carbohydrates, as described above, due to their extreme affinity for water, cannot be crystallized anhydrous in all cases. Sugar molecules, monosaccharides as well as oligosaccharides, frequently co-crystallize with water molecules. Here, in turn, more than one crystalline hydrate form may be possible for every single sugar. For example, crystalline glucose is known in an anhydrous as well as in a monohydrate form, sialic acid crystallizes in an anhydrous and a dihydrate form, crystalline lactose is known anhydrous and as a monohydrate and maltose is known anhydrous as well as a monohydrate. In which crystal form or in which polymorph a sugar occurs or is marketed influences its material properties, here to mention are stability, its hygroscopicity as well as its solubility. In addition, crystallization often fails when other components are present in solution, which are chemically similar to the substance to be crystallized, since these prevent a stable three-dimensional orientation of the targeted material in the crystallization process. Especially with sugar mixtures stemming from fermentations this is a common phenomenon. Furthermore, crystallization is a rather slow process, which sometimes, if not run continuously, can take several days per batch, so faster solutions are preferred.

After the crystallization, residual mother liquor needs to be separated off either batchwise or continuously without endangering the crystal integrity and yield. In addition to water and water vapor, water-miscible organic solvents such as alcohols of all kinds and mixtures of water with water-miscible organic solvents are used for separation in combination with mechanical separation using a suction filter or a centrifuge.

In short, while crystallization provides an excellent means of isolating sugars before drying, crystallization parameters have not yet been identified for any conceivable saccharide neither its industrial applicability has been shown. Furthermore, the crystal mass has to be washed, which entails additional stress and contamination of the sugar mass and generally reduces the yield before the crystalline mass finally is ready to be dried.

The second method of drying is spray drying. Spray drying is a method of producing a dry powder from a liquid or slurry by means of a hot gas flow. Thermally-sensitive materials such as foods and pharmaceuticals can be dried in this way as heat contact time is rather short, whereby spray drying ensures a consistent particle size distribution. In most cases air is the heated drying medium; however, nitrogen can be used when inert conditions are necessary. Spray dryers use some type of atomizer or spray nozzle to disperse the liquid or slurry into a controlled drop size spray. The dry powder often has the advantage to be free-flowing. Some of the disadvantages of spray drying are that there is a risk of a dust explosion and it has a high energy requirement as well as a high demand for air. Spray drying is a pure drying method rather than a purification technique by which no purification is achieved in comparison to crystallization.

Another method of drying is freeze-drying. Freeze drying, also known as lyophilization or cryodesiccation, is a low temperature dehydration process that involves freezing the product, lowering the pressure, and then removing the ice by sublimation. Freeze drying results in a high-quality product because of the low temperature used in the process. The original shape of the product is maintained and quality of the rehydrated product is excellent in most cases. Primary applications of freeze drying include biological, biomedical, and food processing as well as preservation. Like spray drying, freeze-drying does not result in product purification, but only in its anhydrous formulation. Some disadvantages of this method are that it requires a high energy input, a great deal of time in contrast to other types of drying and the large surface. The ready product produced by freeze-drying is increased in its susceptibility to water absorbency.

A special method of drying is the spray freeze-drying or freeze spray-drying method, where the material to be dried is sprayed into for example liquid nitrogen in forming small ice-particles, which are subsequently dried by sublimation in a freeze-drying process. This ultimately results in freeze-dried, globular particles. However, this method is hard to apply to industrial scale due to the high energy requirements.

Band or belt drying is the next method to be discussed. The band dryer is a thermal process apparatus for continuously drying and cooling of all possible suspensions as well as food masses with the aid of air, inert gas or flue gas. The band dryer or band cooler is an apparatus for a particularly gentle product treatment. The wet material is fed continuously and evenly in an inlet chamber and usually passes through the drying chambers on horizontally arranged, perforated drying belts. It is flowed through by hot gases. The drying room is divided into several chambers, each of which can be equipped with a circulating air fan and a heating coil. Each dryer cell can be controlled individually. The product flow rates of the drying/cooling air can be varied in each cell. In addition, the transport speed of the material to be dried can be varied, thus providing an additional parameter for adjusting the drying time of the material. The heating or cooling of the cells can be done directly or indirectly, with all heating media such as oil, steam, hot water or hot gases. The disadvantages of this method are the difficult downsizing and inhomogeneous product discharge. The additional application of vacuum to this process can generally speed it up and drive it under milder conditions. This extends the potential product portfolio to materials that are too sensitive for a standard vacuum band drying process. Therefore, vacuum band drying is declared an independent process. The disadvantage would lay in the additional engineering difficulty to build the band chambers airtight and vacuum compatible.

To overcome all the drawbacks from the known drying methods, the present invention provides a roller drying or drum drying method, which is simple, cost effective and scalable, for the drying of human milk oligosaccharides.

The method of roller or drum drying of the present invention for drying human milk oligosaccharides, represents a simpler, safer and more energy efficient method. And it is particularly relevant for the drying of HMOs which need a special care for drying due to their properties. This method does not need a heated air flow and there is no risk of dust explosions or electrical charge due to circulating material flow.

SUMMARY

The present invention concerns a simple and economical process for drying HMOs. The drying of saccharides, oligo- and polysaccharides in particular, and above all the drying of HMOs is a very special undertaking in which many parameters must be taken into consideration. HMOs are very sensitive substances, which are intended for the pharmaceutical or food industry and are therefore heavily regulated and to which high quality demands are made.

It is an object of the present invention to provide a roller drying or a drum drying method to dry human milk oligosaccharides and make them available as a solid.

As an additional embodiment, the present invention relates to vacuum roller drying or vacuum drum drying applied to HMOs.

It is yet another object of the present invention to provide a method of roller drying or drum drying for HMOs where the quality of such HMOs is obtained with maintained purity due to the mild drying conditions of such method. Where HMOs with a specific water content, a specific surface texture as well as a certain particle size is obtained, which gives such HMOs unique product properties for the pharmaceutical and food industry.

It is another object of the present invention to provide an industrial scale method of roller drying or drum drying for HMOs. Specifically, the method should be suitable for providing dried HMOs ranging from kg-scale to tons-scale.

DETAILED DESCRIPTION

Figure 1:
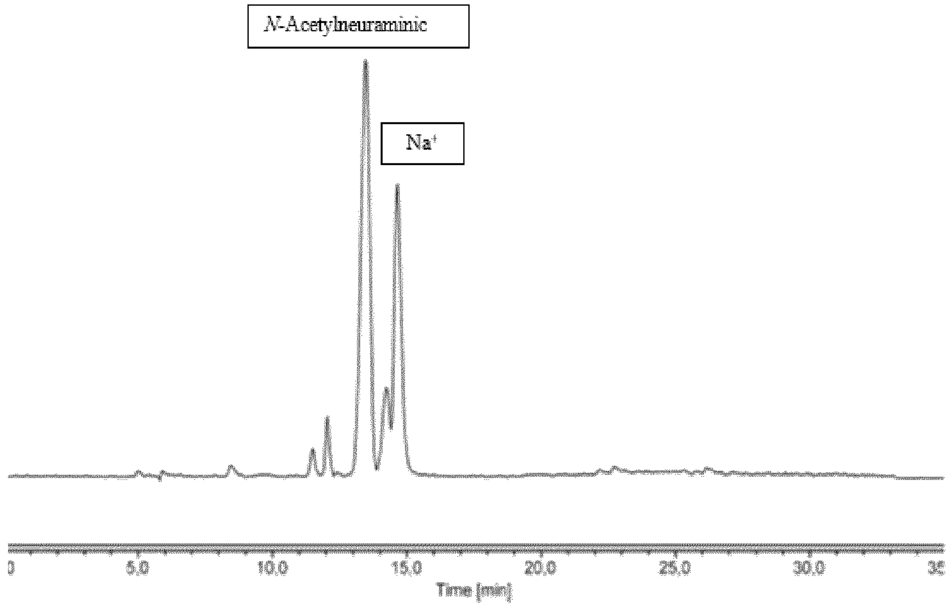
FIG. 1 shows a HILIC-CAD (Hydrophilic interaction liquid chromatography coupled to a charged aerosol detector) spectrum of the N-acteylneuraminic acid sodium salt used as starting material in examples 1 and 2.
Figure 2:
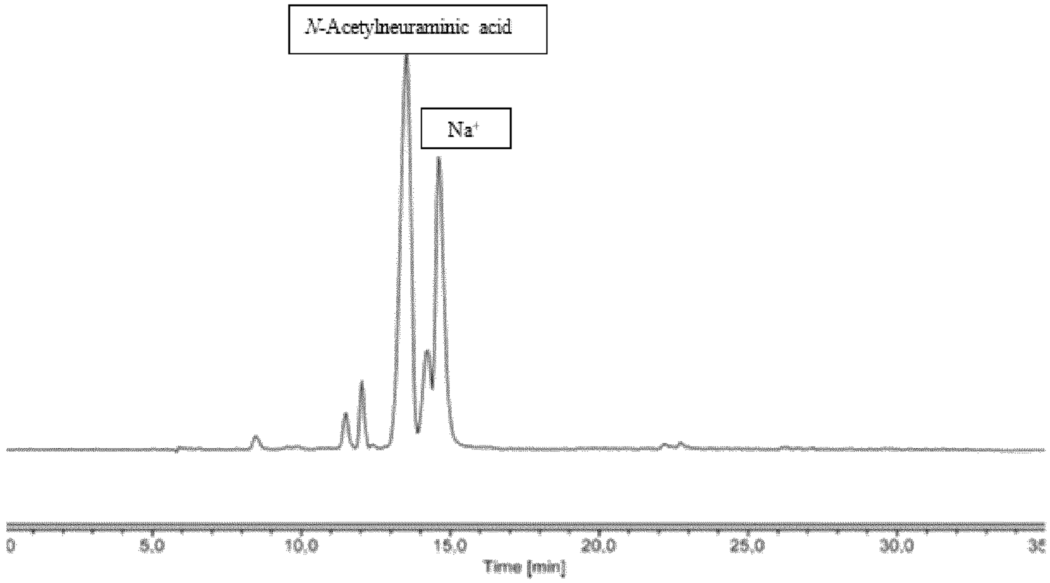
FIG. 2 shows a HILIC-CAD (Hydrophilic interaction liquid chromatography coupled to a charged aerosol detector) spectrum of the N-acteylneuraminic acid sodium salt obtained as a product in example 1.
Figure 3:
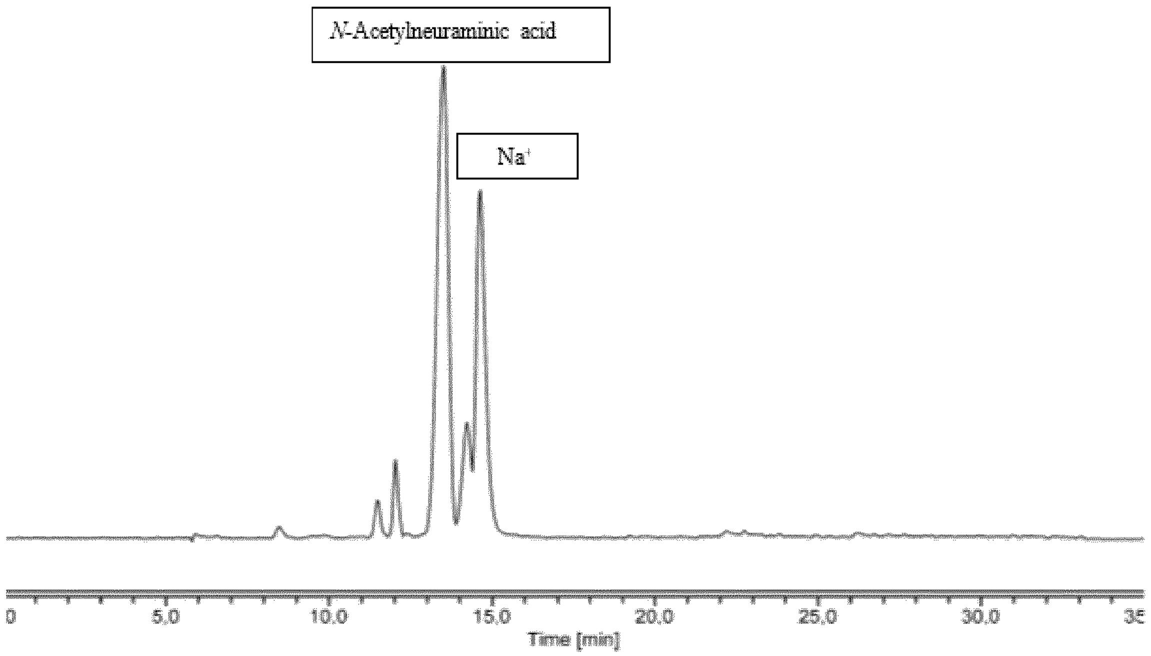
FIG. 3 shows a HILIC-CAD (Hydrophilic interaction liquid chromatography coupled to a charged aerosol detector) spectrum of the N-acteylneuraminic acid sodium salt obtained as a product in example 2.
Figure 4:
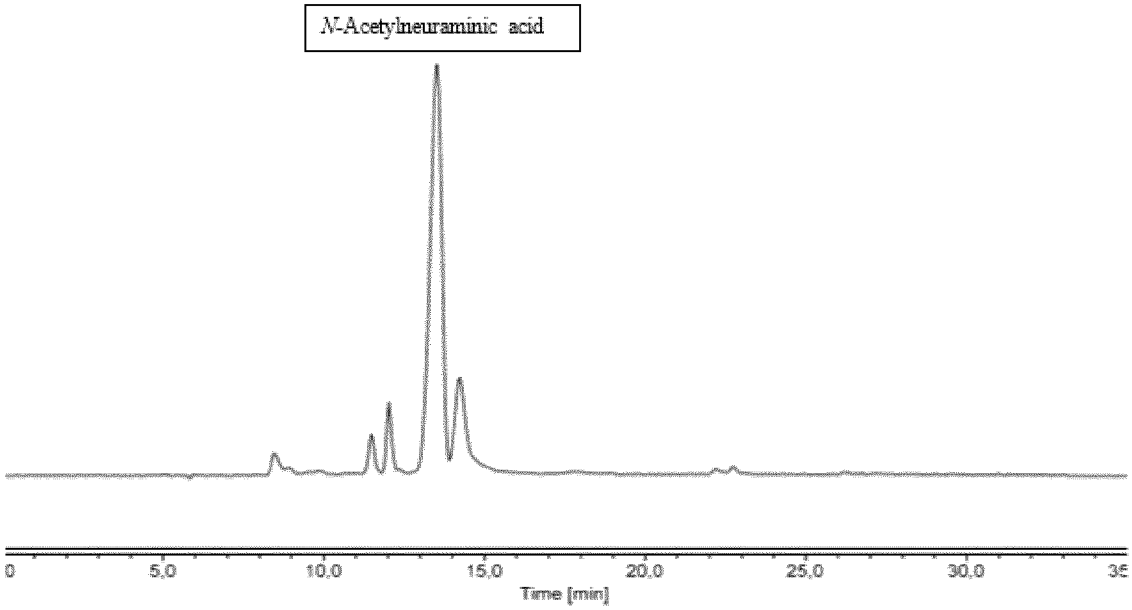
FIG. 4 shows a HILIC-CAD (Hydrophilic interaction liquid chromatography coupled to a charged aerosol detector) spectrum of the N-acteylneuraminic acid used as a starting material in example 3.
Figure 5:
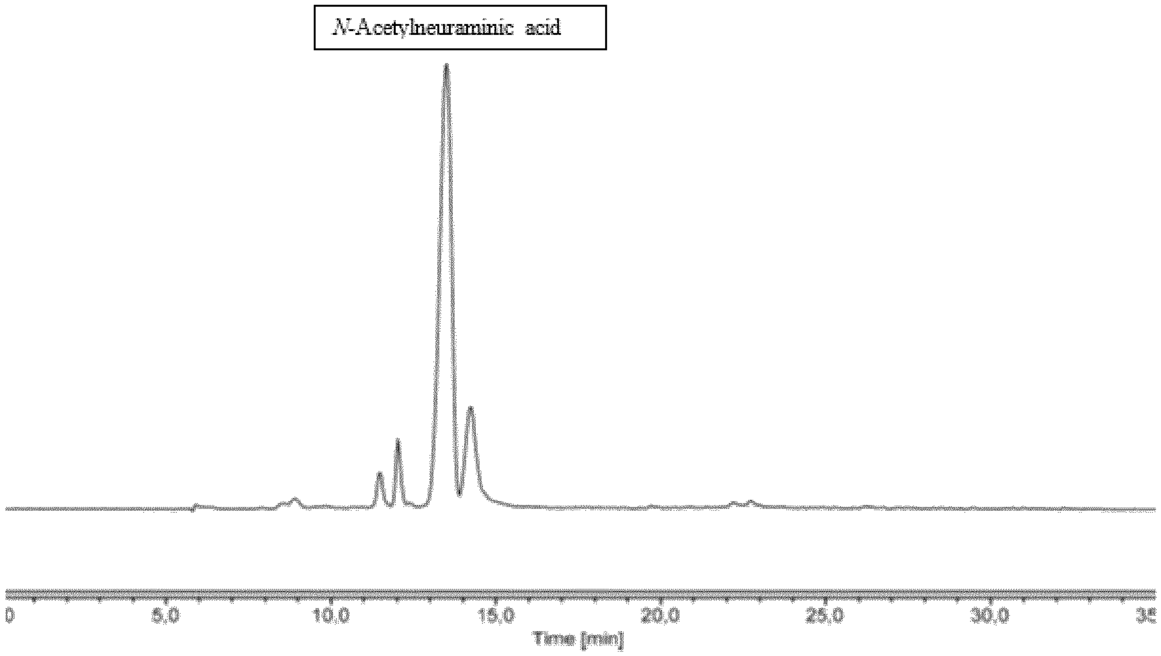
FIG. 5 shows a HILIC-CAD (Hydrophilic interaction liquid chromatography coupled to a charged aerosol detector) spectrum of the N-acteylneuraminic acid obtained as a product in example 3.
Figure 6:
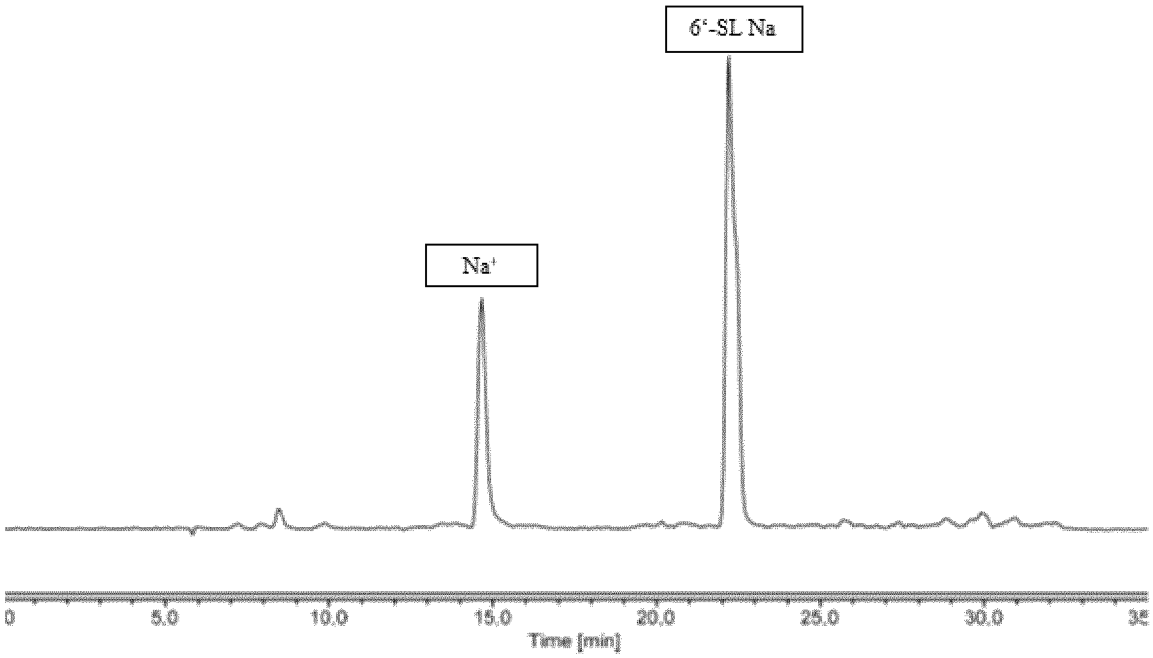
FIG. 6 shows a HILIC-CAD (Hydrophilic interaction liquid chromatography coupled to a charged aerosol detector) spectrum of the 6'-sialyllactose sodium salt used as a starting material in example 5.
Figure 7:
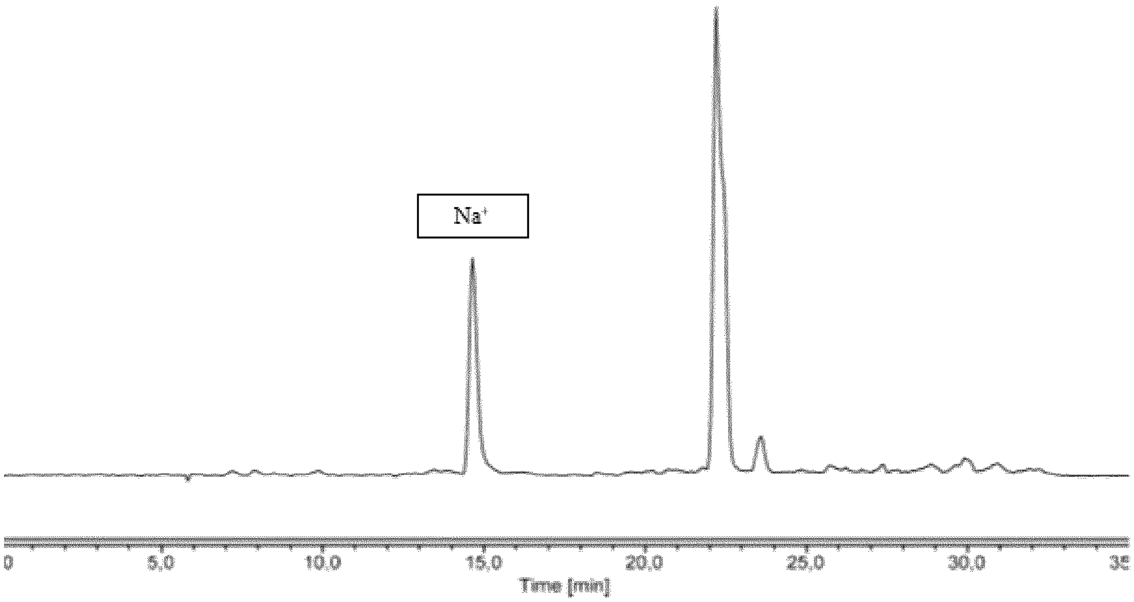
FIG. 7 shows a HILIC-CAD (Hydrophilic interaction liquid chromatography coupled to a charged aerosol detector) spectrum of the 6'-sialyllactose sodium salt obtained as a product in example 5.
Figure 8:
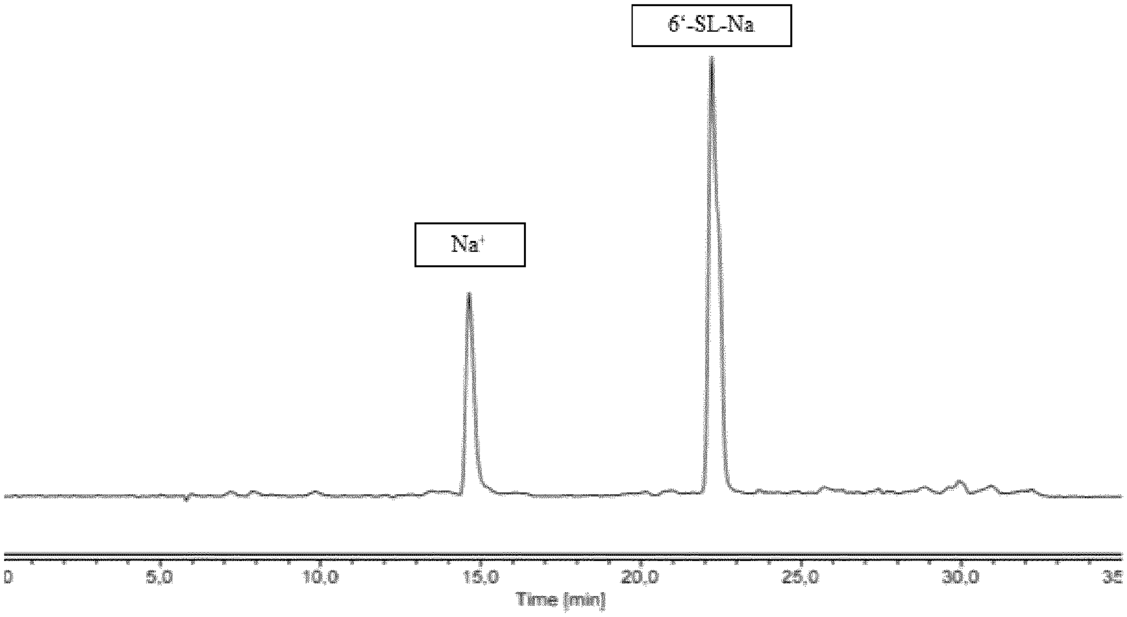
FIG. 8 shows a HILIC-CAD (Hydrophilic interaction liquid chromatography coupled to a charged aerosol detector) spectrum of the 6'-sialyllactose sodium salt used as a starting material in example 6.
Figure 9:
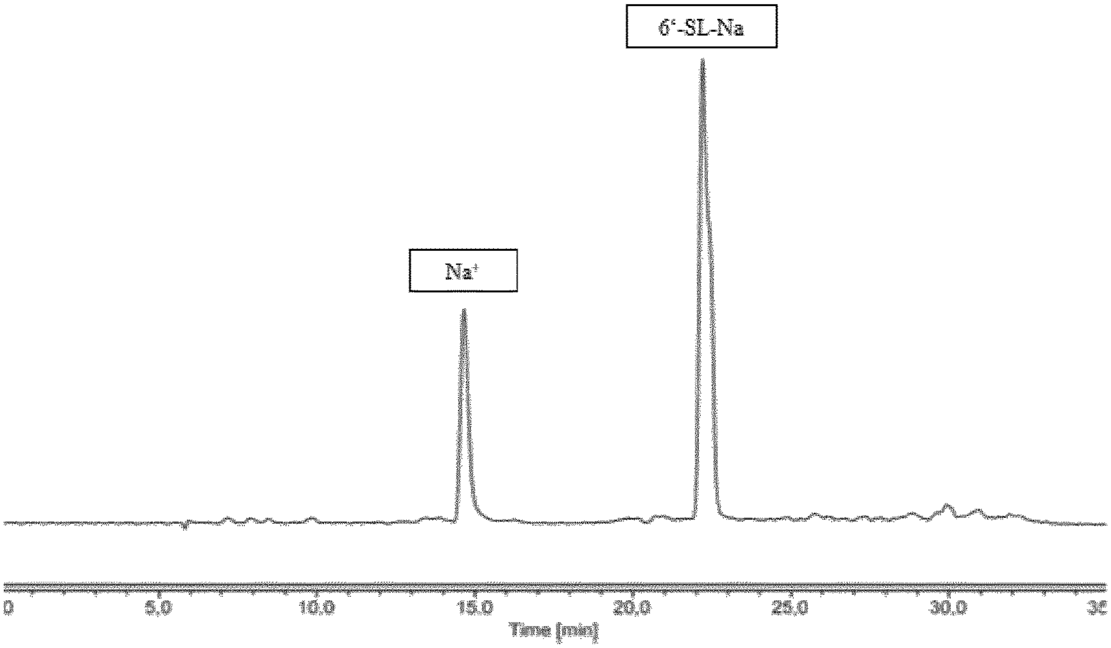
FIG. 9 shows a HILIC-CAD (Hydrophilic interaction liquid chromatography coupled to a charged aerosol detector) spectrum of the 6'-sialyllactose sodium salt obtained as a product in example 6.
Figure 10:
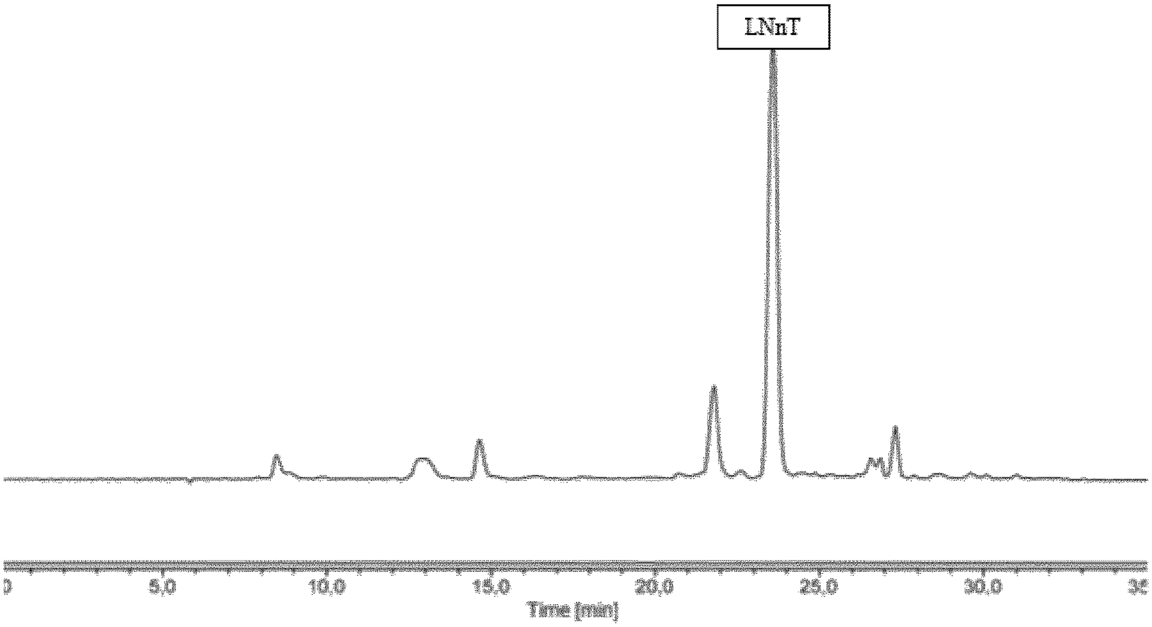
FIG. 10 shows a HILIC-CAD (Hydrophilic interaction liquid chromatography coupled to a charged aerosol detector) spectrum of the lacto-N-neotetraose used as a starting material in example 7.
Figure 11:
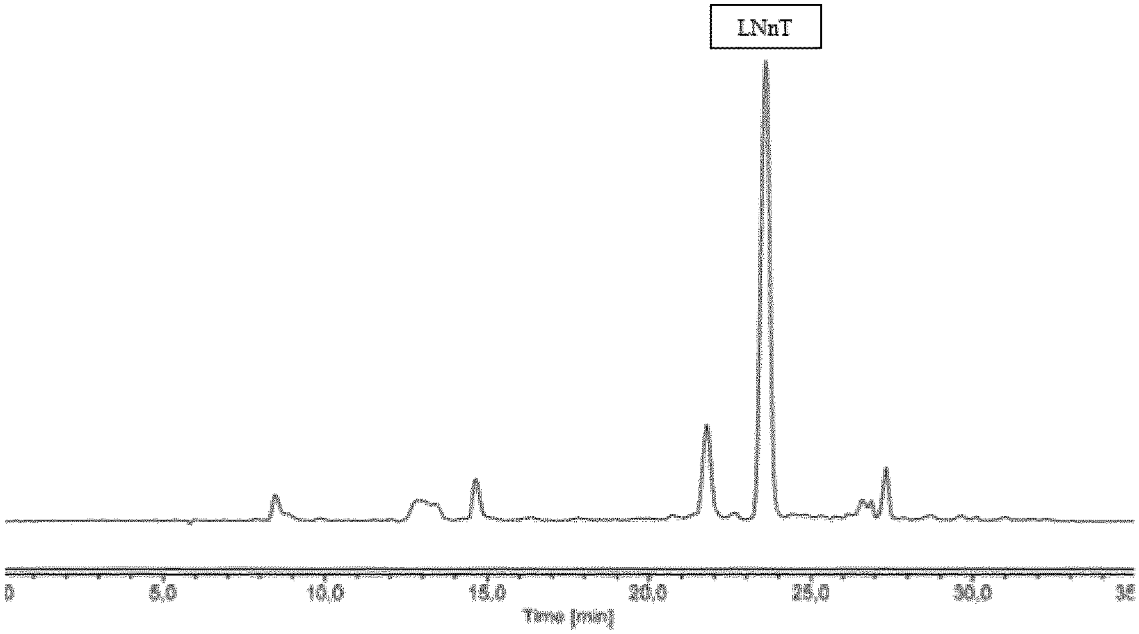
FIG. 11 shows a HILIC-CAD (Hydrophilic interaction liquid chromatography coupled to a charged aerosol detector) spectrum of the lacto-N-neotetraose obtained as a product in example 7.
Figure 12:
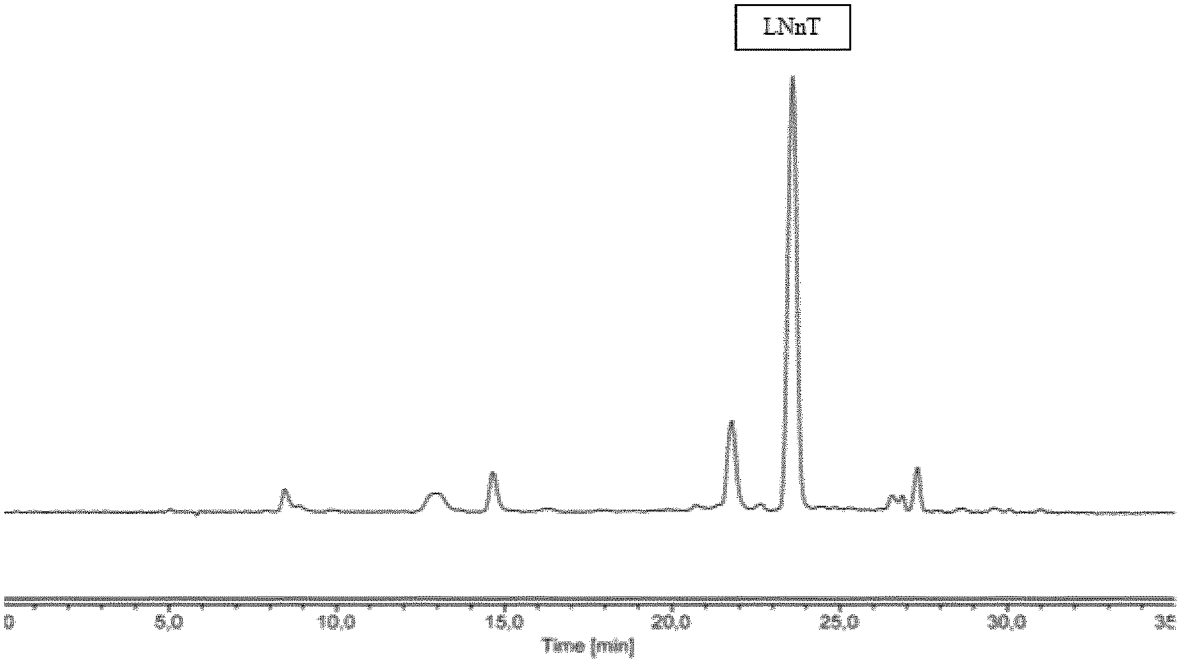
FIG. 12 shows a HILIC-CAD (Hydrophilic interaction liquid chromatography coupled to a charged aerosol detector) spectrum of the lacto-N-neotetraose used as a starting material in example 8.
Figure 13:
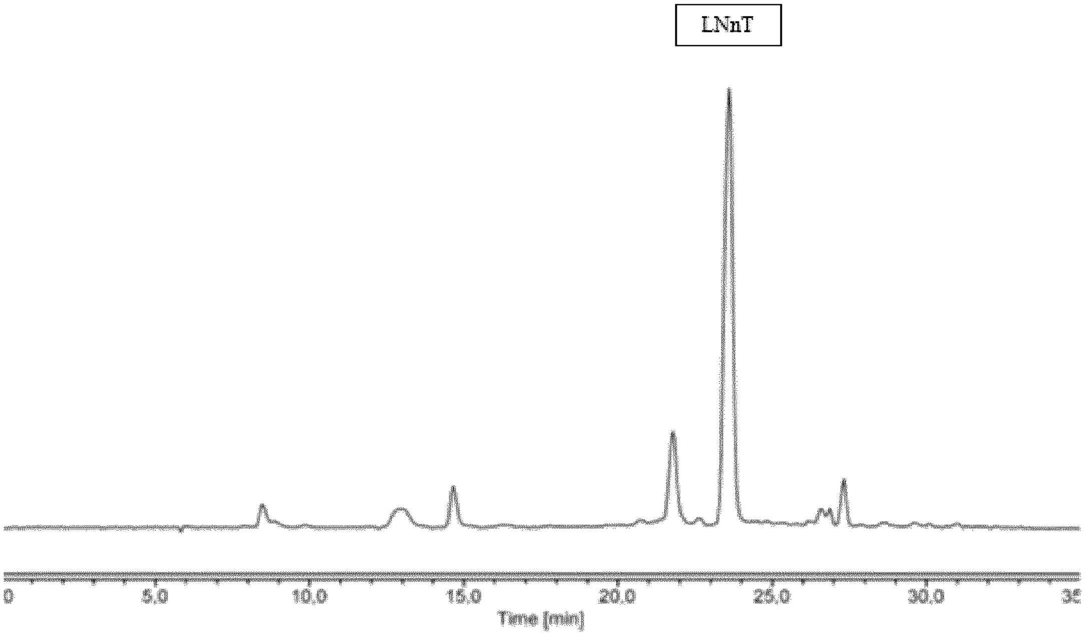
FIG. 13 shows a HILIC-CAD (Hydrophilic interaction liquid chromatography coupled to a charged aerosol detector) spectrum of the lacto-N-neotetraose obtained as a product in example 8.
Figure 14:
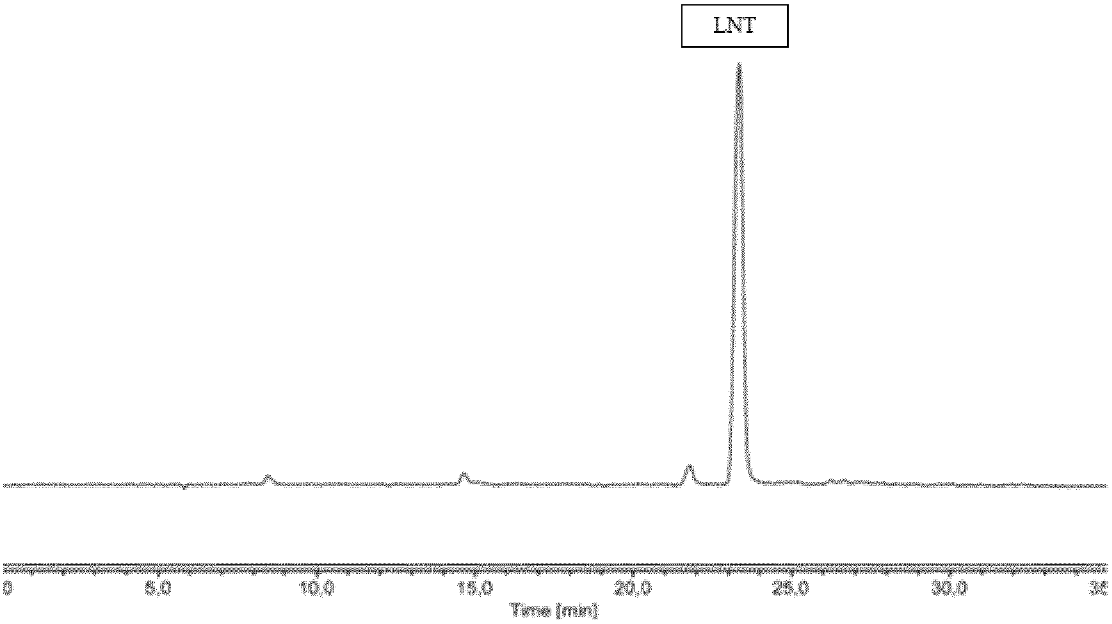
FIG. 14 shows a HILIC-CAD (Hydrophilic interaction liquid chromatography coupled to a charged aerosol detector) spectrum of the lacto-N-tetraose used as a starting material in example 9.
Figure 15:
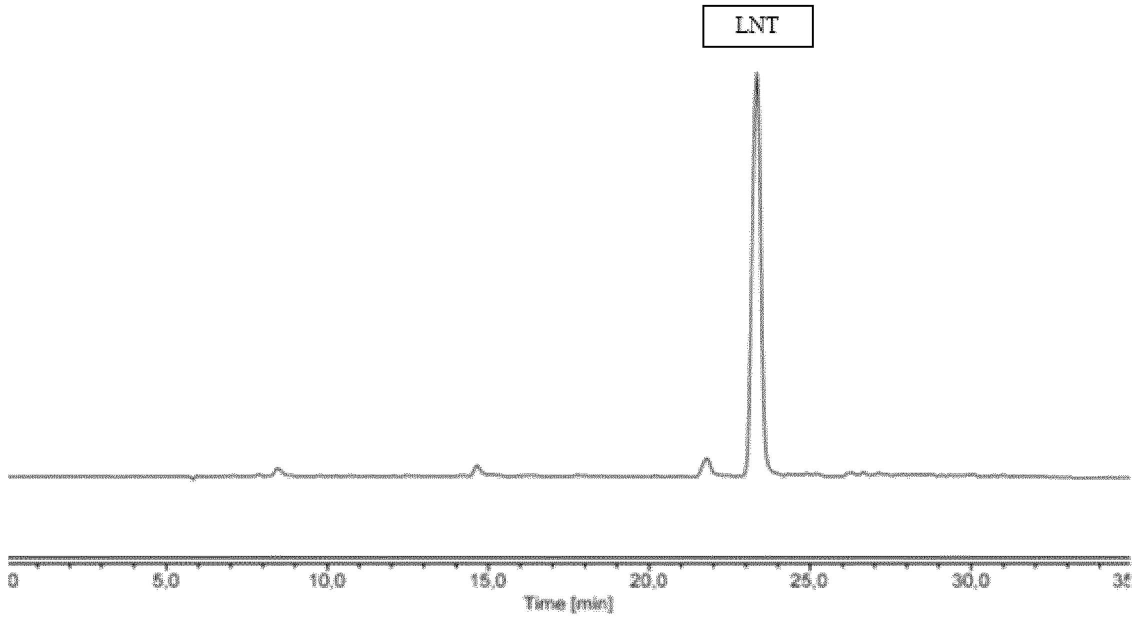
FIG. 15 shows a HILIC-CAD (Hydrophilic interaction liquid chromatography coupled to a charged aerosol detector) spectrum of the lacto-N-tetraose obtained as a product in example 9.
Figure 16:
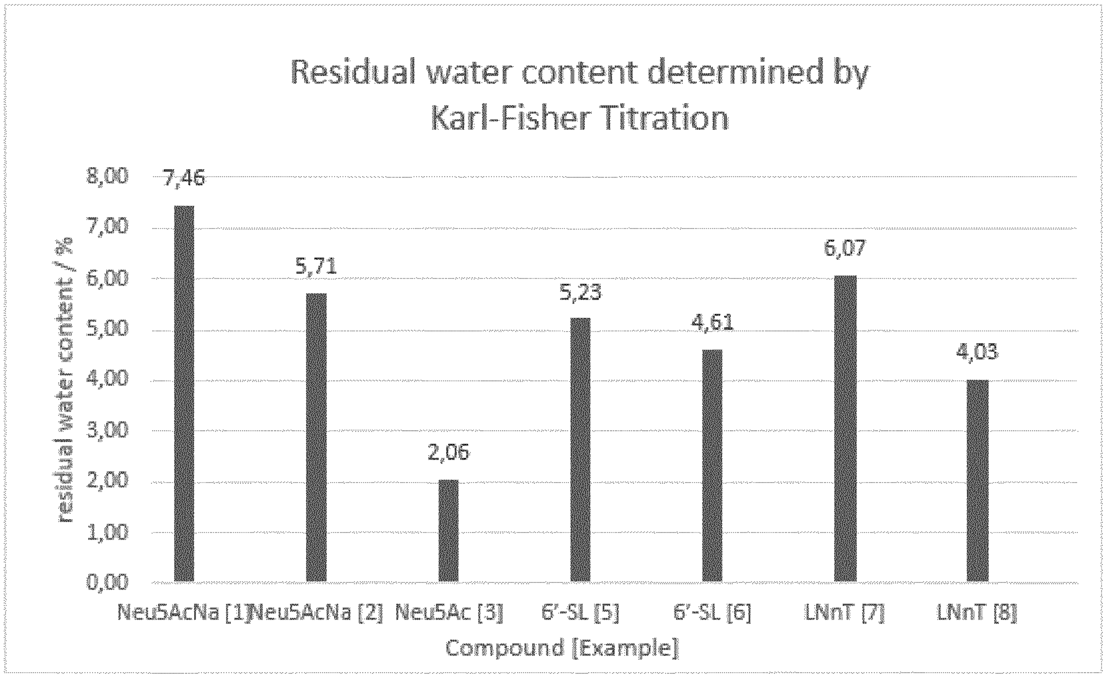
FIG. 16 shows residual water content as a function of the drying parameters of selected examples.
Figure 17:
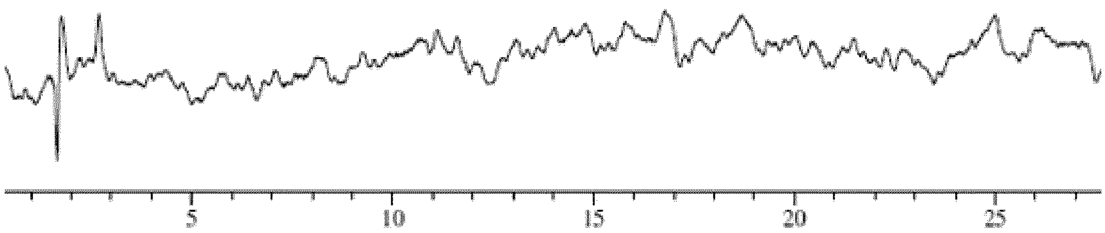
FIG. 17 shows a HPAEC-PAD (High performance anion exchange chromatography with pulsed amperometric detection) spectrum of water.
Figure 18:
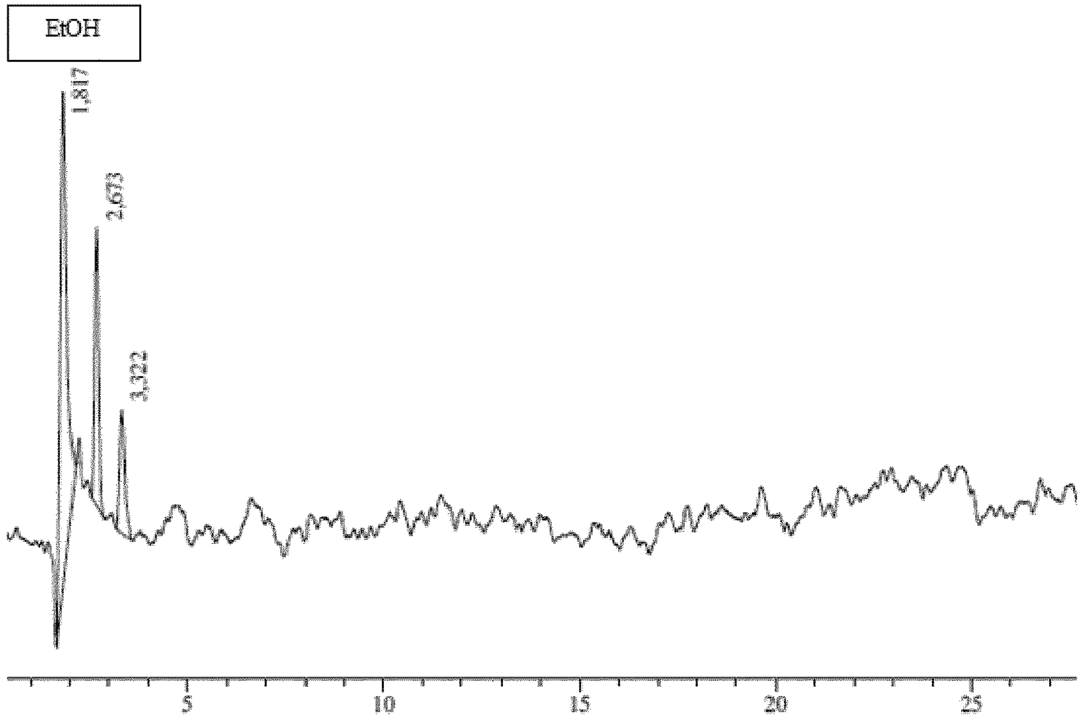
FIG. 18 shows a HPAEC-PAD (High performance anion exchange chromatography with pulsed amperometric detection) spectrum of Ethanol in water.
Figure 19:
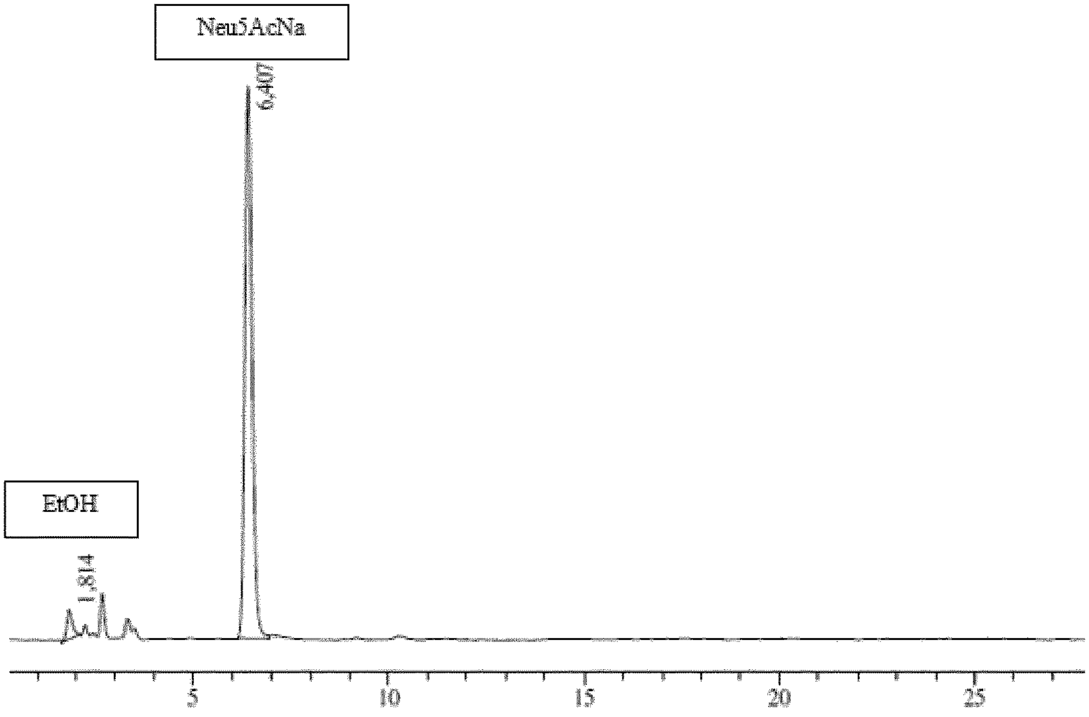
FIG. 19 shows a HPAEC-PAD (High performance anion exchange chromatography with pulsed amperometric detection) spectrum of N-acteylneuraminic acid sodium salt used as starting material in example 2.
Figure 20:
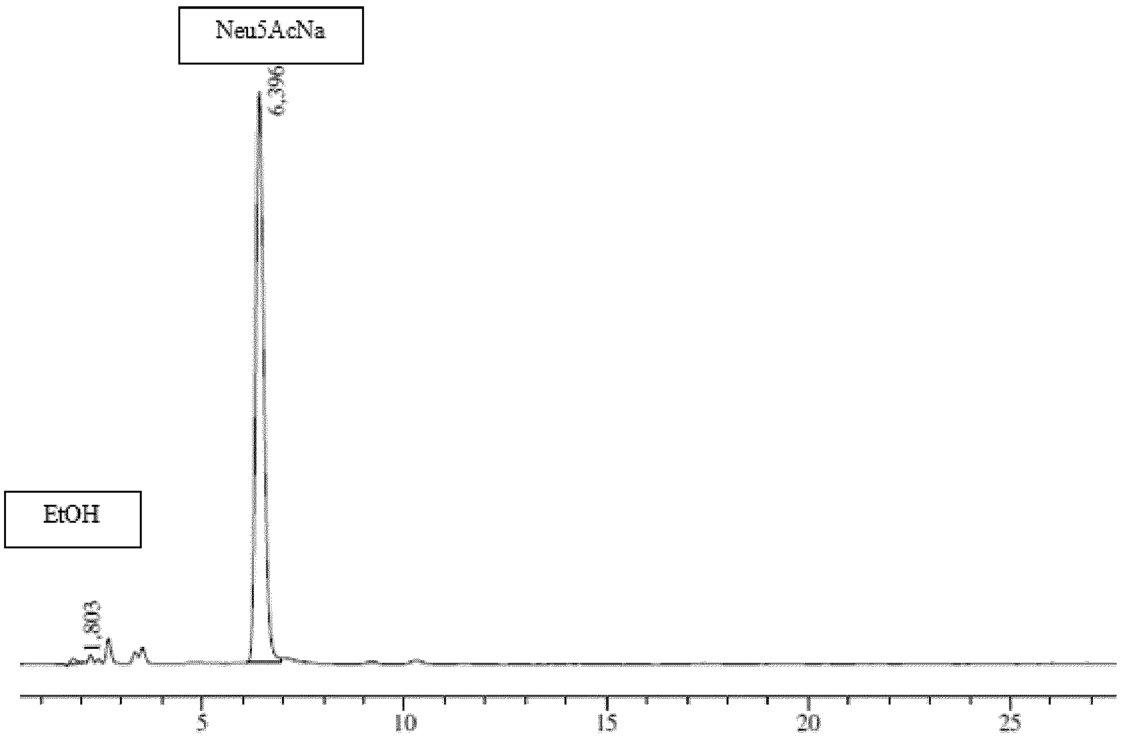
FIG. 20 shows a HPAEC-PAD (High performance anion exchange chromatography with pulsed amperometric detection) spectrum of N-acteylneuraminic acid sodium salt obtained as product in example 2.
Figure 21:
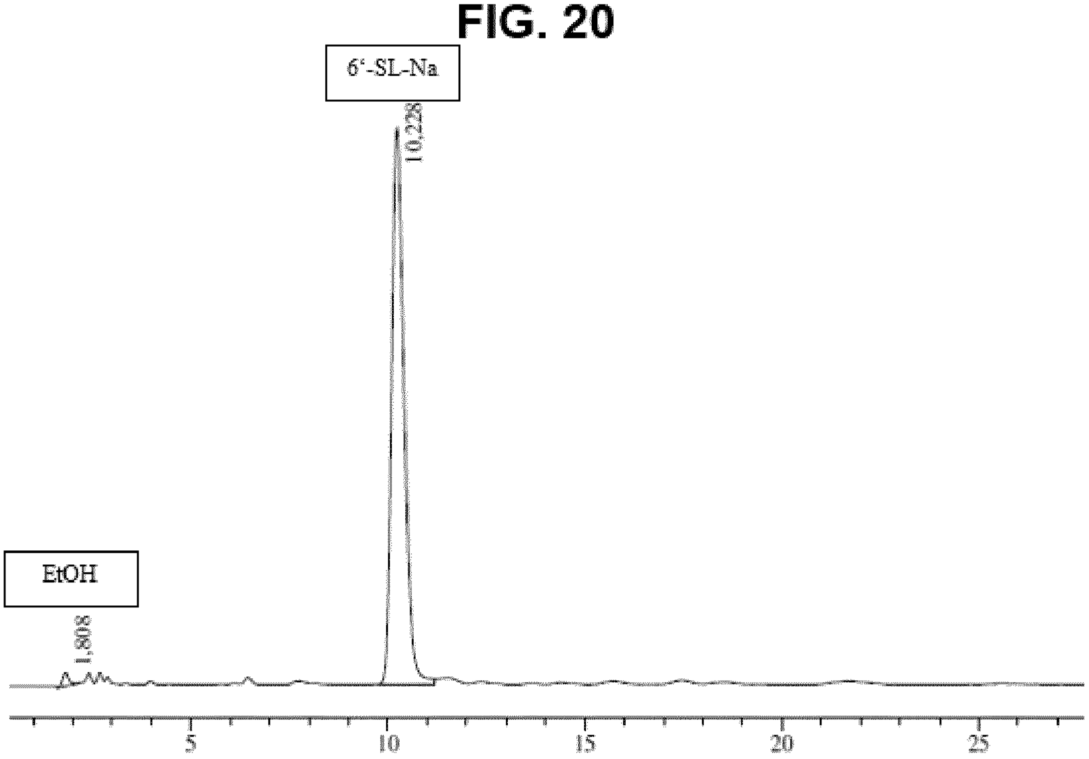
FIG. 21 shows a HPAEC-PAD (High performance anion exchange chromatography with pulsed amperometric detection) spectrum of 6'-sialyllactose sodium salt used as a starting material in example 6.
Figure 22:
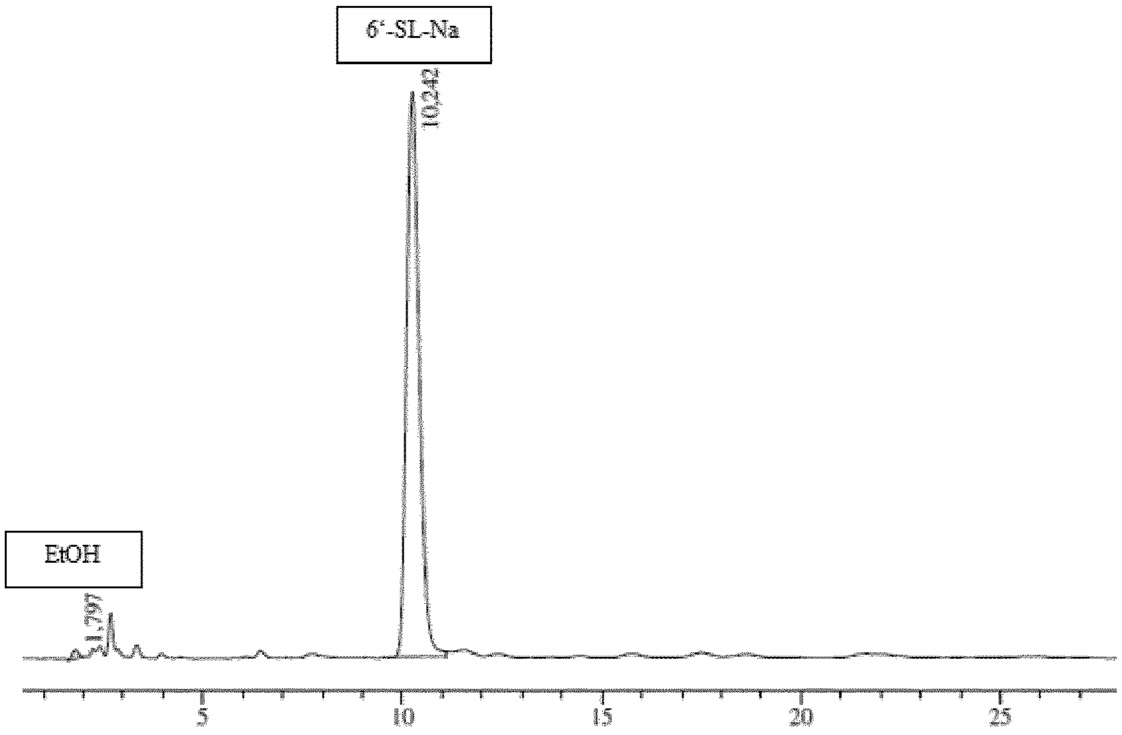
FIG. 22 shows a HPAEC-PAD (High performance anion exchange chromatography with pulsed amperometric detection) spectrum of 6'-sialyllactose sodium salt obtained as a product in example 6.
Figure 23:
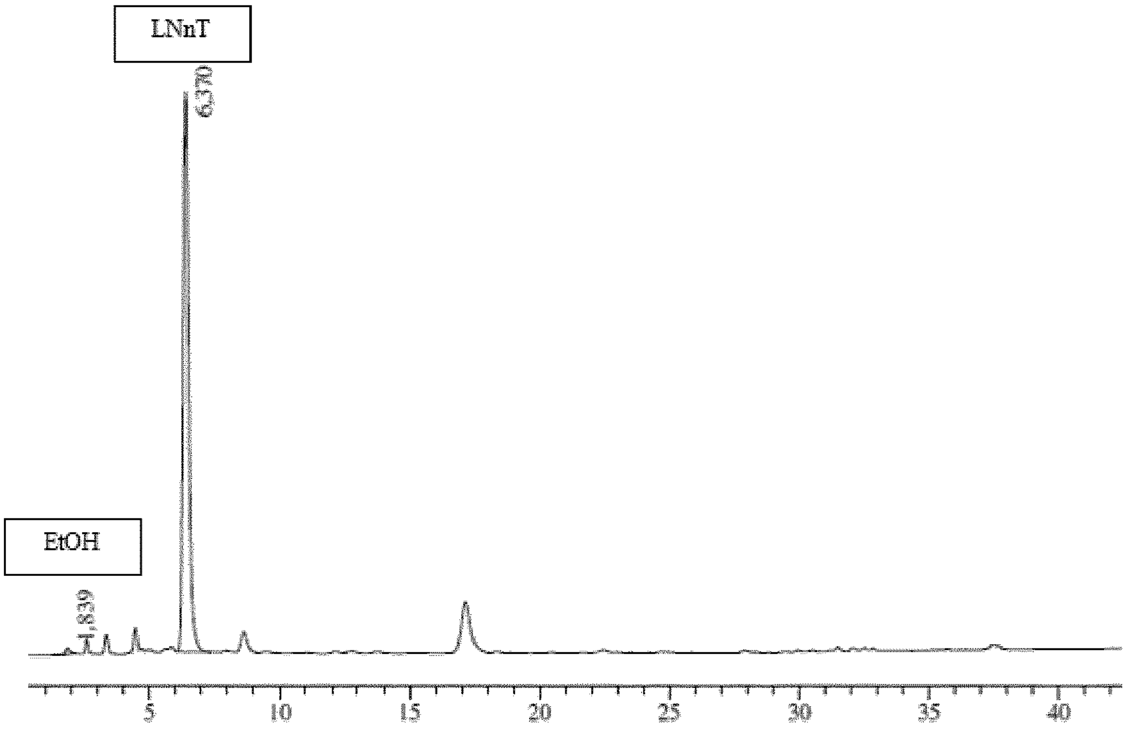
FIG. 23 shows a HPAEC-PAD (High performance anion exchange chromatography with pulsed amperometric detection) spectrum of lacto-N-neotetraose used as a starting material in example 9.
Figure 24:
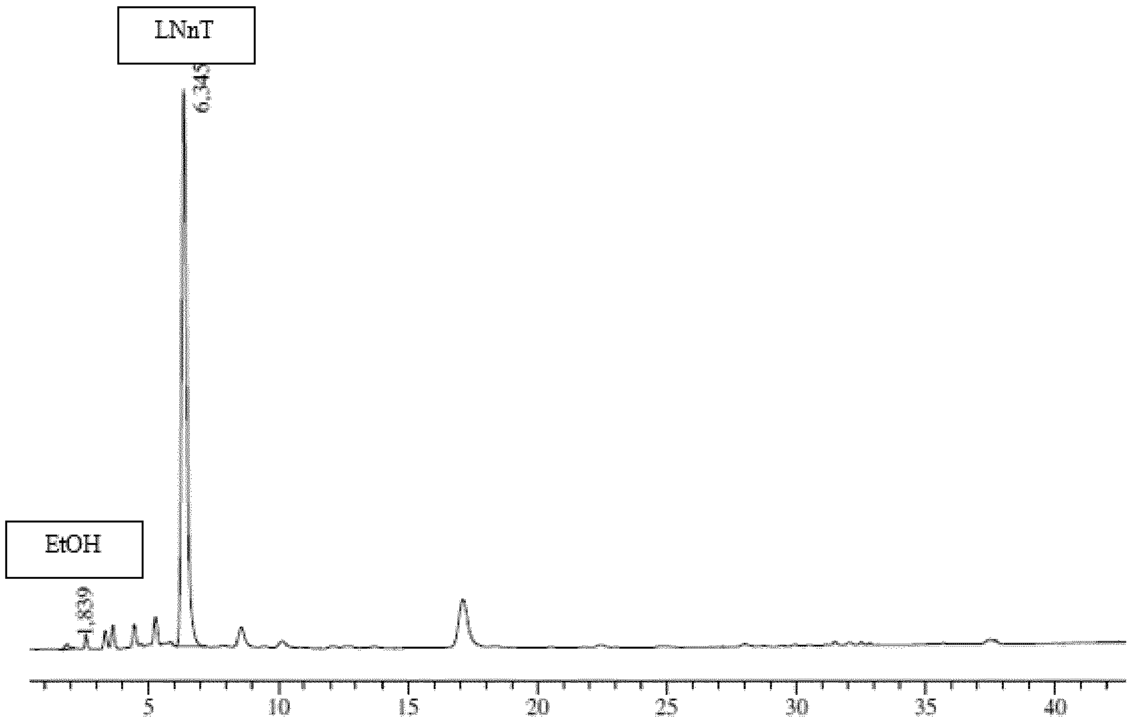
FIG. 24 shows a HPAEC-PAD (High performance anion exchange chromatography with pulsed amperometric detection) spectrum of lacto-N-neotetraose obtained as a product in example 9.
Figure 25:
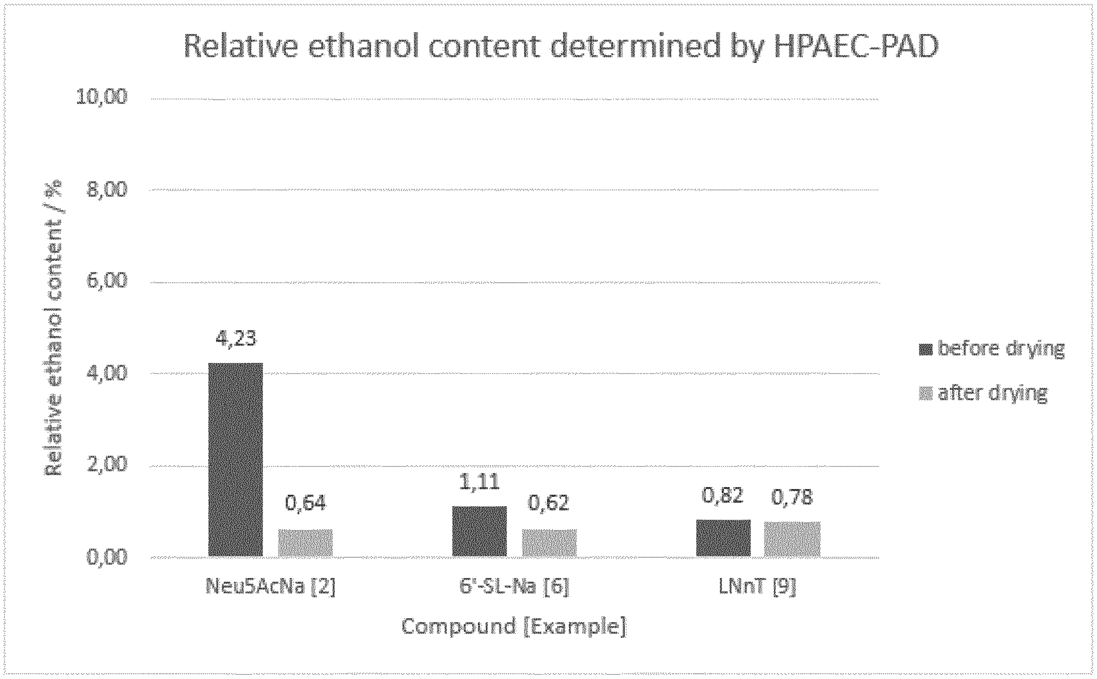
FIG. 25 shows relative ethanol content determined by HPAEC-PAD (High performance anion exchange chromatography with pulsed amperometric detection) after drying as a result of the ethanol content before drying of selected examples.

A human milk oligosaccharide is provided from a microbial fermentation to a roller drying or drum drying to obtain a human milk oligosaccharide in the form of a powder.

The present invention provides a method for drying human milk oligosaccharides and/or for obtaining human milk oligosaccharides in the form of a powder, the method comprises the steps of:

a) providing an aqueous solution containing a purified human milk oligosaccharide;
b) applying the aqueous solution to a roller dryer or a drum dryer.

The HMO used in such drying method may be produced by microbial fermentation, wherein a genetically-engineered microorganism that is able to synthesize the desired HMO is cultivated in a culture medium (fermentation broth) and under conditions that are permissive for the synthesis of the desired HMO by said genetically-engineered microorganism.

The purification of the HMO produced by microbial fermentation comprises the step of separating the microbial cells from the fermentation broth to obtain a cleared process stream which is essentially free of cells and which contains the desired HMO. This step is the first step in the process of purifying the desired oligosaccharides. The purification of the HMO from a fermentation broth mentioned above, includes one or more of the following:

i) removing the microbial cells from the fermentation broth to obtain a cleared process stream;
ii) subjecting the cleared process stream to at least one ultrafiltration;
iii) treating the cleared process stream at least one time with a cation exchange resin and/or at least one time with an anion exchange resin;
iv) subjecting the cleared process stream to at least one nanofiltration;
v) subjecting the cleared process stream to at least one electrodialysis;
vi) treating the cleared process stream at least one time with activated charcoal; and/or
vii) subjecting the cleared process stream at least one time to a crystallization and/or precipitation step.

Suitable methods for removing the microbial cells from the fermentation broth include centrifugation wherein the microbial cells are obtained as a pellet and the fermentation broth as a supernatant. In an additional and/or alternative embodiment, the microbial cells are removed from the fermentation broth by means of filtration. Suitable filtration methods for removing the cells from the fermentation broth include microfiltration and ultrafiltration.

Microfiltration as such is a physical filtration process where a particle-containing fluid is passed through a special pore-sized membrane to separate the particles from the fluid. The term “microfiltration” as used herein refers to a physical filtration process where cells are separated from the fermentation broth.

Ultrafiltration is a variety of membrane filtration and is not fundamentally different. In ultrafiltration, forces like pressure or concentration gradients lead to a separation through a semipermeable membrane. Cells, suspended solids and solutes of high molecular weight are retained in the so-called retentate, while water and low molecular weight solutes such as the desired HMO pass through the membrane in the permeate (filtrate). Ultrafiltration membranes are defined by the molecular weight cut-off (MWCO) of the membrane used. Ultrafiltration is applied in cross-flow or dead-end mode.

Typically, the microbial cells synthesize the desired HMO intracellularly and secrete it into the fermentation broth. The thus produced HMO ends up in the fermentation broth which is then subjected to further process steps for the purification of the HMO as described herein after.

Notwithstanding that the process is used for the purification of an HMO that has been produced by microbial fermentation, said process may also be employed to purify an HMO that was produced by enzymatic catalysis in-vitro. The HMO can be purified from the reaction mixture at the end of the biocatalytic reaction. Said reaction mixture is subjected to the process for the purification as a cleared process stream.

The cleared process stream contains the HMO as well as by-products and undesired impurities such as, for example, monosaccharides, disaccharides, undesired oligosaccharide by-products, ions, amino acids, polypeptides, proteins and/or nucleic acids.

In an additional and/or alternative embodiment, the process for the purification of the desired HMO comprises the step of at least one cation exchange treatment to remove positively charged compounds from the cleared process stream. Suitable cation exchange resins for removing positively charged compounds include Lewatit S2568 (H+) (Lanxess AG, Cologne, DE).

In an additional and/or alternative embodiment, the process for the purification of the desired HMO comprises the step of an anion exchange treatment to remove undesired negatively charged compounds from the cleared process stream. Suitable anion exchange resins include Lewatit S6368 A, Lewatit S4268, Lewatit S5528, Lewatit 56368A (Lanxess AG. Cologne, DE), Dowex AG 1×2 (Mesh 200-400), Dowex 1×8 (Mesh 100-200), Purolite Chromalite CGA100×4 (Purolite GmbH, Ratingen, Del.), Dow Amberlite FPA51 (Dow Chemicals, MI, USA).

In as additional/or alternative embodiment, the process for the purification of the HMO comprises a nanofiltration and/or a diafiltration step to remove impurities having a lower molecular weight, and to concentrate the desired oligosaccharides. Diafiltration involves the addition of fresh water to a solution in order to remove (wash out) membrane-permeable components. Diafiltration can be used to separate components on the basis of their molecular size and charge by using appropriate membranes, wherein one or more species are efficiently retained and other species are membrane permeable. In particular, diafiltration using a nanofiltration membrane is effective for the separation of low molecular weight compounds like small molecules and salts. Nanofiltration membranes usually have a molecular weight cut-off in the range 150-1000 Daltons. Nanofiltration is widely used in the dairy industry for the concentration and demineralization of whey.

Suitable membranes for nanofiltration and/or diafiltration include Dow Filmtec NF270-4040, Trisep 4040-XN45-TSF (Microdyn-Nadir GmbH, Wiesbaden, DE), GE4040F30 and GH4040F50 (GE Water & Process Technologies, Ratingen, DE).

Diafiltration using nanofiltration membranes was found to be efficient as a pretreatment to remove significant amounts of contaminants prior to electrodialysis treatment of the solution containing the oligosaccharide. The use of nanofiltration membranes for concentration and diafiltration during the purification of HMOs results in lower energy and processing costs, and better product quality due to reduced thermal exposure, leading to reduced Maillard reactions and aldol reactions.

In an additional and/or alternative embodiment, the process for the purification of the HMO comprises at least one electrodialysis step. Electrodialysis (ED) is used to transport salt ions from one solution through ion-exchange membranes to another solution under the influence of an applied electric potential difference and it can be used for the separation or concentration of ions in solutions based on their selective electromigration through semipermeable membranes.

The basic principle of electrodialysis consists of an electrolytic cell comprising a pair of electrodes submerged into an electrolyte for the conduction of ions, connected to a direct current generator. The electrode connected to the positive pole of the direct current generator is the anode, and the electrode connected to the negative pole is the cathode. The electrolyte solution then supports the current flow, which results from the movement of negative and positive ions towards the anode and cathode, respectively. The membranes used for electrodialysis are essentially sheets of porous ion-exchange resins with negative or positive charge groups, and are therefore described as cationic or anionic membranes, respectively. The ion-exchange membranes are usually made of polystyrene carrying a suitable functional group (such as sulfonic acid for cationic membranes or a quaternary ammonium group for anionic membranes) cross-linked with divinylbenzene. The electrolyte can be, for example, sodium chloride, sodium acetate, sodium propionate or sulfamic acid. The electrodialysis stack is then assembled in such a way that the anionic and cationic membranes are parallel as in a filter press between two electrode blocks, such that the stream undergoing ion depletion is well separated from the stream undergoing ion enrichment (the two solutions are also referred to as the dilute (undergoing ion depletion) and concentrate (undergoing ion enrichment). The heart of the electrodialysis process is the membrane stack, which consists of several anion-exchange membranes and cation-exchange membranes separated by spacers, installed between two electrodes. By applying a direct electric current, anions and cations will migrate across the membranes towards the electrodes.

In an additional and/or alternative embodiment, the process for the purification of the HMO further comprises a step of continuous chromatography like simulated bed moving (SMB) chromatography. Simulated moving bed (SMB) chromatography originated in the petrochemical and mineral industries. Today, SMB chromatography is used by the pharmaceutical industry to isolate enantiomers from racemic mixtures. Large-scale SMB chromatography has already been used for the separation of the monosaccharide fructose from fructose-glucose solutions and for the separation of the disaccharide sucrose from sugar beet or sugar cane syrups.

SMB processes used to separate saccharides use e.g. calcium charged, cross-linked polystyrene resins, anion resins in the bisulfite form (Bechthold M., et al., Chemie Ingenieur Technik, 2010, 82, 65-75), or polystyrenic gel strong acid cation resin in the hydrogen form (Purolite PCR833H) (Purolite, Bala Cynwyd, USA).

Given the continuous mode of operation, the recycling of the mobile phase and also the potential to use large column sizes, SMB systems can in principle be scaled to achieve production volumes of hundreds of tons.

The process step of simulated moving bed chromatography is advantageous in that this process step allows further removal of oligosaccharides being structurally closely related to the desired oligosaccharide.

In an additional and/or alternative embodiment, the process for the purification of the HMO comprises a treatment of the process stream with activated charcoal to remove contaminating substances such as colorants from the process stream.

In additional and/or alternative embodiment, the process for the purification of the HMO comprises at least one step of crystallization or precipitation of the HMO from the cleared process stream. Crystallization or precipitation of the HMO from the process stream may be performed by adding a suitable amount of an organic solvent that is miscible with water to the process stream containing the HMO. The organic solvent may be selected from the group consisting of C1- to C6-alcohols and C1- to C4-carbon acids.

An additional and/or alternative embodiment of the process for the purification of the aimed HMO comprises a step of sterile filtration and/or endotoxin removal, preferably by filtration of the process stream through a 3 kDa filter or 6 kDa filter.

In an additional and/or alternative embodiment, the process for the purification of the HMO comprises a step of increasing the concentration of the HMO in the process stream. The concentration of the HMO in the process stream can be increased by subjecting the process stream to vacuum evaporation, reverse osmosis or nanofiltration (e.g. nanofiltration with a nanofiltration membrane having a size exclusion limit of ≤20 Å). Alternatively, crystallized or precipitated HMO is dissolved in water, to obtain a solution of the HMO possessing the desired concentration of HMO.

In an additional and/or alternative embodiment, the resulting process stream is an aqueous solution which contains the desired HMO in a concentration of ≥1 g/L, ≥10 g/L, ≥20 g/L, ≥25 g/L, ≥30 g/L, ≥40 g/L, ≥60 g/L, ≥100 g/L, ≥200 g/L, ≥300 g/L or even ≥400 g/L.

In an additional and/or alternative embodiment, the aqueous solution contains the HMO in a purity of at least 50%, at least 65%, at least 80%, at least 90%, at least 95% or at least 98% with respect to the weight of dry matter/solutes within such aqueous solution.

The method for obtaining a human milk oligosaccharide in the form of a powder through the use of a vacuum roller dryer or a vacuum drum dryer comprises the step of providing an aqueous solution containing the desired purified HMO.

Such aqueous solution contains the desired HMO in an amount of at least 1% (w/v), 10% (w/v), 20% (w/v), 30% (w/v), 35% (w/v), and up to 45% (w/v), 50% (w/v), or at least 60% (w/v).

Such aqueous solution does not contain genetically-engineered microorganisms, nucleic acid molecules derived from genetically-engineered microorganisms and proteins.

In the process for obtaining an HMO dried powder, the aqueous solution containing the HMO is subjected to a roller drying or drum drying method.

Roller drying or drum drying is a method of drying food, among other things. A solution, a suspension or an emulsion or a mixture thereof is applied to previously heated rollers by means of a nozzle or a gap, before the substance to be dried on the roller usually comes out amorphous, depending on the material also in a crystalline form and then peeled off from the roller surface with a blade. In this method, one or two, in some cases, four rollers are installed in an apparatus which, if at least two rollers are installed, rotate in opposite directions to achieve an increase in the active surface. The ready material comes out mostly amorphous or sometimes crystalline and my form of flakes. In general, the material distinguishes by its particular form of drying of a similar material, which is obtained for example from a crystallization, spray drying or freeze-drying process in its water content, its hygroscopicity, its flowability and other physicochemical properties such as porosity or density.

In a particular embodiment, the additional application of vacuum to this method can generally speed it up so that it can be driven under milder conditions and the aimed, dried material can be obtained with a lower water content. This extends the potential product portfolio to materials that are too sensitive for a standard vacuum roller or drum drying method, like for example human milk oligosaccharides.

Roller drying or drum drying is a method for obtaining dry powders, wherein the solution containing the substance of interest (e.g. any kind of human milk oligosaccharide) is applied dropwise into a gap made between heated drum cylinders. The drums cylinders are usually heated with steam or thermal oil. The aqueous solution containing the HMO is distributed evenly on the heated drum cylinders and the moisture content evaporates during the partial rotation of such drum cylinders. After the aqueous solution is dried, it is removed by a scraper from the drum cylinders, falling as a powder on a tray.

There are many types of roller dryers or drum dryers depending on the configuration of the drum cylinders. Drum dryers comprise at least one drum cylinder. The drum body of the drum or drums of a drum dryer are heated. Typically, the drum body is heated from the inside by steam.

In one embodiment, the roller or drum dryer has a single drum dryer cylinder. The feed type for single drum dryers is selected from the group consisting of splash-feed or spray-feed, dip-feed, below roll feed, top roll feed, side roll feed and multi roll feed. The splash-feed or spray-feed is made when placing a tank below the drum to feed the liquid. The liquid is splashed to stick on the drum with rotary wings mounted in the liquid tank. The dip-feed is made when providing a shallow bowl-like liquid tanks below the drum. The liquid is fed in this tank. The drum is dipped in the fluid, which is stuck on the drum surface. In the liquid tank, an agitator is provided to prevent precipitation of solid and to keep the liquid density constant. For roll-feed the liquid is fed between the drum and the feed roll to form a film on the drying drum surface and depending on where the feed is located it can be selected from below roll feed, top roll feed, side roll feed and multi roll feed.

In a particular embodiment, the roller or drum dryer is a double drum dryer. In a double drum dryer (two-drum dryer cylinders), wherein two heated drum cylinders are provided, the gap between the cylinders can be adjusted, even during rotation of the cylinders.

In a specific embodiment, the roller or drum drying is operated under vacuum. Vacuum roller drying or vacuum drum drying has the advantage that it is very fast and that the exposure of the substance to be dried using high temperatures is quite short.

The additional embodiment of vacuum roller drying or vacuum drum drying method uses an aqueous solution containing HMOs which is provided onto heated, rotating drum cylinders, in an evacuated chamber. After removal of the solvent, the product is peeled from the drum cylinders either in a continuous or batch-wise manner and obtained as amorphous or crystalline solid material. A high-quality material is obtained with maintained purity due to the mild drying conditions. Furthermore, a material with a specific water content, a specific surface texture as well as a certain particle size is obtained, which gives it unique product properties for the pharmaceutical as well as food industry.

The aqueous solution containing the HMO of interest that has been purified from a fermentation broth or process stream is dried at a drum cylinder wall temperature of at least 25° C., preferably at least 30° C., preferably at least 35° C., preferably at least 40° C., preferably at least 45° C., preferably at least 50° C., preferably at least 55° C., preferably at least 60° C., preferably at least 65° C., preferably at least 70° C., more preferably at least 75° C., and less than 200° C., less than 195° C., less than 190° C., less than 185° C., less than 180° C., preferably less than 175° C., less than 170° C., less than 165° C., less than 160° C., less than 155° C., and more preferably less than 150° C.

The aqueous solution containing the HMO that has been purified from a fermentation broth or process stream is dried at a shell temperature of at least 25° C., preferably at least 30° C., preferably at least 35° C., preferably at least 40° C., preferably at least 45° C., preferably at least 50° C., and less than 150° C., preferably less than 145° C., preferably less than 140° C., preferably less than 135° C., preferably less than 130° C., and more preferably less than 145° C. In a particularly preferred embodiment, the aqueous solution containing the aimed HMO is vacuum roller dried or vacuum drum dried at a shell temperature of about 80° C. to about 90° C.

The aqueous solution containing the HMO that has been purified from a fermentation broth or process stream is dried at a rotation speed of the drum cylinders of at least 0.1 rpm, preferably at least 1.0 rpm and less than 20 rpm, more preferably less than 30 rpm. In a particularly preferred embodiment, the aqueous solution containing the aimed HMO is vacuum roller dried or vacuum drum dried at a rotation speed of the drum cylinders of between 1.5 and 6.5 rpm.

The aqueous solution containing the HMO that has been purified from a fermentation broth or process stream is dried at a gap between the drum cylinders of at least 0.02 mm, preferably at least 0.2 mm, and less than 20 mm, more preferably less than 10 mm. In a particularly preferred embodiment, the aqueous solution containing the aimed HMO is vacuum roller dried or vacuum drum dried at a gap width of between 0.02 and 2 mm.

The aqueous solution containing the HMO that has been purified from a fermentation broth or process stream is dried at a pressure of at least 0.55 mbar, preferably at least at 5.5 mbar, and less than 1013 mbar, more preferably less than 550 mbar. In a particularly preferred embodiment, the aqueous solution containing the aimed HMO is vacuum roller dried or vacuum drum dried at a pressure of 55 mbar.

In an additional and/or alternative embodiment, the aqueous solution containing the HMO that has been purified from a fermentation broth or process stream is dried from a solution with an ethanol content of at least 0.1% (v/v), preferably at least of 1.0% (v/v), and less than 100% (v/v), more preferably less than 50% (v/v). In a particularly preferred embodiment, the aqueous solution containing the aimed HMO is vacuum roller dried or vacuum drum dried from a solution with an ethanol content of 10-50% (v/v).

In an additional and/or alternative embodiment, the aqueous solution containing the HMO that has been purified from a fermentation broth or process stream is dried from a solution with a relative ethanol content determined by HPAEC-PAD of at least 0.01%, preferably at least of 0.1%, and less than 100%, more preferably less than 10%. In a particularly preferred embodiment, the aqueous solution containing the aimed HMO is vacuum roller dried or vacuum drum dried from a solution with a relative ethanol content determined by HPAEC-PAD of 0.5-5.0%.

In an additional and/or alternative embodiment, the aqueous solution containing the HMO that has been purified from a fermentation broth or process stream is dried resulting in a product with a relative ethanol content determined by HPAEC-PAD of at least 0.01%, preferably at least of 0.1%, and less than 100%, more preferably less than 10%. In a particularly preferred embodiment, the aqueous solution containing the aimed HMO is vacuum roller dried or vacuum drum dried resulting in a dried HMO with a relative ethanol content determined by HPAEC-PAD of 0.5-1.0%.

The vacuum roller drying or vacuum drum drying of the aqueous solution containing the HMO provides a powder of low hygroscopicity, wherein the HMO is present in amorphous form, and wherein the particle size is homogeneous.

The vacuum roller dried or vacuum drum dried powder containing the HMO that has been purified from a process stream is used for the manufacture of a nutritional composition. The vacuum roller dried or vacuum drum dried powder consisting of the HMO is suitable for human consumptions and may thus be included into preparations for human consumption such as medicinal formulations, infant formula, dairy drinks or dietary supplements.

The HMO may be a neutral HMO, preferably selected from the group consisting of 2'-fucosyllactose (2'-FL), 3-fucosyllactose (3-FL), 2',3-difucosyllactose (DiFL), lacto-N-tetraose (LNT), lacto-N-neotetraose (LNnT), and lacto-N-fucopentaose I (LNFPI). In an additional and/or alternative embodiment, the at least one additional HMO may be a sialylated HMO, preferably selected from the group consisting of 3'-sialyllactose (3'-SL), 6'-sialyllactose (6'-SL), sialyllacto-N-tetraose (LST)-a, LST-b, LST-c and disialyllacto-N-tetraose (DSLNT).

The present invention is described with respect to particular embodiments and with reference to drawings, but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description and drawings provided herein, numerous specific details are set forth. However, it is understood that embodiments of the invention may be practiced without these specific details. In other instances, well-known methods, structures and techniques have not been shown in detail in order not to obscure an understanding of this description.

The invention is described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

EXAMPLES

Example 1: Drying of N-Acetylneuraminic Acid Sodium Salt from Aqueous Solution The drum cylinder wall temperature of the vacuum drum dryer was set to 105° C. and the shell temperature to 85° C. The vacuum was set to 55 mbar, the roll speed to 2.5 rpm and the gap width to 2.0 mm. A solution of N-acetylneuraminic acid sodium salt in water was prepared with a DSC of 25.0%. The solution was applied dropwise into the gap of the heated drum cylinders which were set to rotate in opposite directions. The material began immediately to dry on the drum cylinders and was removed with the help of blades. After complete addition the vacuum was released to atmospheric pressure and the drum cylinder wall temperature was set to room temperature. A fine white powder was obtained with a residual water content of 7.46% determined by Karl-Fisher-Titration.

Example 2: Drying of N-Acetylneuraminic Acid Sodium Salt from Ethanolic Solution The drum cylinder wall temperature of the vacuum drum dryer was set to 120° C. and the shell temperature was set to 85° C. The vacuum was set to 55 mbar, the roll speed to 3.5 rpm and the gap width to 2.0 mm. A solution of N-acetylneuraminic acid sodium salt in water with a content of 50% EtOH was prepared resulting in a DSC of 6.9%. HPAEC-PAD of the starting material shows a relative ethanol content of 4.06%. The solution was applied dropwise into the gap of the heated drum cylinders which were set to rotate in opposite directions. The material began immediately to dry on the drum cylinders and was removed with the help of blades. After complete addition the vacuum was released to atmospheric pressure and the drum cylinder wall temperature was set to room temperature. A white fine powder was obtained with a residual water content of 5.71% determined by Karl-Fisher-Titration. HPAEC-PAD of the dried product shows a relative ethanol content of 0.64%.

Example 3: Drying of N-Acetylneuraminic Acid from Aqueous Solution

The drum cylinder wall temperature of the vacuum drum dryer was set to 85° C. and the shell temperature was set to 85° C. The vacuum was set to 55 mbar, the roll speed to 3.0 rpm and the gap width to 2.0 mm. A solution of N-acetylneuraminic acid free acidic form in water was prepared with a DSC of 3.6%. The solution was applied dropwise into the gap of the heated drum cylinders which were set to rotate in opposite directions. The material began immediately to dry on the drum cylinders and was removed with the help of blades. After complete addition the vacuum was released to atmospheric pressure and the drum cylinder wall temperature was set to room temperature. A slightly pinkish fine powder was obtained with a residual water content of 2.05% determined by Karl-Fisher-Titration.

Example 4: Drying of 2'-Fucosyllactose from Aqueous Solution

The drum cylinder wall temperature of the vacuum drum dryer was set to 100° C. and the shell temperature was set to 85° C. The vacuum was set to 55 mbar, the roll speed to 2.5 rpm and the gap width to 2.0 mm. A solution of 2'-fucosyllactose in water was prepared with a DSC of 45.0%. The solution was applied dropwise into the gap of the heated drum cylinders which were set to rotate in opposite directions. The material began immediately to dry on the drum cylinders and was removed with the help of blades. After complete addition the vacuum was released to atmospheric pressure and the drum cylinder wall temperature was set to room temperature. An ivory gritty powder was obtained with a residual water content of 4.53% determined by Karl-Fisher-Titration.

Example 5: Drying of 6'-Sialyllactose Sodium Salt from Aqueous Solution

The drum cylinder wall temperature of the vacuum drum dryer was set to 105° C. and the shell temperature was set to 85° C. The vacuum was set to 55 mbar, the roll speed to 3.5 rpm and the gap width to 2.0 mm. A solution of 6'-sialyllactose sodium salt in water was prepared with a DSC of 26.2%. The solution was applied dropwise into the gap of the heated drum cylinders which were set to rotate in opposite directions. The material began immediately to dry on the drum cylinders and was removed with the help of blades. After completion of the addition the vacuum was released to atmospheric pressure and the drum cylinder wall temperature was set to room temperature. A slightly yellow fine powder was obtained with a residual water content of 5.23% determined by Karl-Fisher-Titration.

Example 6: Drying of 6'-Sialyllactose Sodium Salt from Ethanolic Solution

The drum cylinder wall temperature of the vacuum drum dryer was set to 105° C. and the shell temperature was set to 85° C. The vacuum was set to 55 mbar, the roll speed to 4.5 rpm and the gap width to 2.0 mm. A solution of 6'-sialyllactose sodium salt in water with a content of 10% EtOH was prepared resulting in a DSC of 26.4%. HPAEC-PAD of the starting material shows a relative ethanol content of 1.10%. The solution was applied dropwise into the gap of the heated drum cylinders which were set to rotate in opposite directions. The material began immediately to dry on the drum cylinders and was removed with the help of blades. After complete addition the vacuum was released to atmospheric pressure and the drum cylinder wall temperature was set to room temperature. A slightly yellow powder was obtained with a residual water content of 4.61% determined by Karl-Fisher-Titration. HPAEC-PAD of the dried product shows a relative ethanol content of 0.62%.

Example 7: Drying of Lacto-N-Neotetraose from Aqueous Solution

The drum cylinder wall temperature of the vacuum drum dryer was set to 105° C. and the shell temperature was set to 85° C. The vacuum was set to 55 mbar, the roll speed to 2.5 rpm and the gap width to 2.0 mm. A solution of lacto-N-neotetraose in water was prepared with a DSC of 21.8%. The solution was applied dropwise into the gap of the heated drum cylinders which were set to rotate in opposite directions. The material began immediately to dry on the drum cylinders and was removed with the help of blades. After complete addition the vacuum was released to atmospheric pressure and the drum cylinder wall temperature was set to room temperature. A white fine powder was obtained with a residual water content of 6,07% determined by Karl-Fisher-Titration.

Example 8: Drying of Lacto-N-Neotetraose from Ethanolic Solution

The drum cylinder wall temperature of the vacuum drum dryer was set to 105° C. and the shell temperature was set to 85° C. The vacuum was set to 55 mbar, the roll speed to 5.5 rpm and the gap width to 2.0 mm. A solution of lacto-N-neotetraose in water with a content of 10% EtOH was prepared resulting in a DSC of 27.3%. The solution was applied dropwise into the gap of the heated drum cylinders which were set to rotate in opposite directions. The material began immediately to dry on the drum cylinders and was removed with the help of blades. After complete addition the vacuum was released to atmospheric pressure and the drum cylinder wall temperature was set to room temperature. A white fine powder was obtained with a residual water content of 4.03% determined by Karl-Fisher-Titration.

Example 9: Drying of Lacto-N-Tetraose from Ethanolic Solution

The drum cylinder wall temperature of the vacuum drum dryer was set to 105° C. and the shell temperature was set to 85° C. The vacuum was set to 55 mbar, the roll speed to 6.5 rpm and the gap width to 2.0 mm. A solution of lacto-N-tetraose in water with a content of 10% EtOH was prepared resulting in a DSC of 17.6%. HPAEC-PAD of the starting material shows a relative ethanol content of 0.81%. The solution was applied dropwise into the gap of the heated drum cylinders, which were set to rotate in opposite directions. The material began immediately to dry on the drum cylinders and was removed with the help of blades. After completion of the addition the vacuum was released to atmospheric pressure and the drum cylinder wall temperature was set to room temperature. A slightly yellow powder was obtained with a residual water content of 5.26% determined by Karl-Fisher-Titration. HPAEC-PAD of the dried product shows a relative ethanol content of 0.77%.

TABLE 1

Residual water content depending on the drying parameters

| Compound [from example X] | DSC [%] | Cylinder Wall Temp. [° C.] | Turns [1/min] | EtOH content in solution [%] | Residual water by KFT [%] | Average residual water by KFT [%] |
|---|---|---|---|---|---|---|
| Neu5Ac-Na [1] | 25.0 | 105 | 2.5 | 0 | 1. 7.458<br>2. 7.469 | 7.464 |
| Neu5Ac-Na [2] | 6.6 | 120 | 3.5 | 50 | 1. 5.729<br>2. 5.685 | 5.707 |
| Neu5Ac [3] | 3.6 | 85 | 3.0 | 0 | 1. 2.069<br>2. 2.040 | 2.055 |
| 2'-FL [4] | 45.0 | 120 | 2.5 | 0 | 1. 4.626<br>2. 4.428 | 4.527 |
| 6'-SL-Na [5] | 26.2 | 105 | 3.5 | 0 | 1. 5.078<br>2. 5.285 | 5.232 |
| 6'-SL-Na [6] | 26.4 | 105 | 4.5 | 10 | 1. 4.527<br>2. 4.684 | 4.606 |
| LNnT [7] | 21.8 | 105 | 2.5 | 0 | 1. 6.004<br>2. 6.138 | 6.070 |
| LNnT [8] | 27.3 | 105 | 2.5 | 10 | 1. 3.958<br>2. 4.100 | 4.030 |
| LNT [9] | 17.6 | 105 | 6.5 | 10 | 1. 5.289<br>2. 5.236 | 5.263 |

TABLE 2

Relative ethanol content after drying as a result of the ethanol content before drying determined via HPAED-PAD

| Compound [from example X] | Relative EtOH area (%) | Relative Carbohydrate area (%) | Relative EtOH content (%) |
|---|---|---|---|
| Neu5Ac-Na before drying [2] | 4.06 | 95.94 | 4.23 |
| Neu5Ac-Na after drying [2] | 0.64 | 99.36 | 0.64 |
| 6'-SL-Na before drying [6] | 1.10 | 98.90 | 1.11 |
| 6'-SL-Na after drying [6] | 0.62 | 99.38 | 0.62 |
| LNnT before drying [8] | 0.81 | 99.19 | 0.82 |
| LNnT after drying [8] | 0.77 | 99.23 | 0.78 |

The invention claimed is:

1. A method for drying human milk oligosaccharides and/or for obtaining human milk oligosaccharides in the form of a powder, comprising:

a) providing an aqueous solution comprising a purified human milk oligosaccharide in a total purity of at least 80% with respect to the weight of dry matter/solutes within the aqueous solution and wherein the aqueous solution has an ethanol content of at least 0.1% (v/v) and less than 100% (v/v); and b) applying the aqueous solution to a roller dryer or a drum dryer wherein the roller dryer or the drum dyer is a vacuum roller dryer or vacuum drum dryer and the aqueous solution is dried at a pressure of at least 5.5 mbar, and less than 550 mbar.

2. The method of claim 1, wherein the aqueous solution comprises the purified human milk oligosaccharide in a concentration of ≥1 g/L.

3. The method of claim 1, wherein the roller dryer or the drum dryer is a single or a double roller dryer or a single or a double drum dryer.

4. The method of claim 1, wherein the aqueous solution is dried at a drum cylinder wall temperature of at least 25° C. and less than 200° C.

5. The method of claim 1, wherein the aqueous solution is dried at a shell temperature of at least 25° C. and less than 150° C.

6. The method of claim 1, wherein the aqueous solution is dried at a rotation speed of the drum cylinders of at least 0.1 rpm and less than 30 rpm.

7. The method of claim 1, wherein the aqueous solution is dried at a gap between the drum cylinders of at least 0.02 mm and less than 20 mm.

8. The method of claim 1, wherein the human milk oligosaccharide is selected from N-acetyl-lactosamines, Lacto-N-biose I, sialylated oligosaccharides, and fucosylated oligosaccharides.

9. The method of claim 8, wherein the N-acetyl-lactosamine or Lacto-N-biose I are selected from one or more of lacto-N-tetraose (LNT), lacto-N-neotetraose (LNnT), and lacto-N-fucopentaose I (LNPFI).

10. The method of claim 8, wherein the sialylated oligosaccharide is selected from one or more of 3'-sialyllactose (3'-SL), 6'-sialyllactose (6'-SL), sialyllacto-N-tetraose a (LST-a), sialyllacto-N-tetraose b (LST-b), sialyllacto-N-tetraose c (LST-c), and disialyllacto-N-tetraose (DSLNT).

11. The method of claim 8, wherein the fucosylated oligosaccharide is selected from one or more of 2'-fucosyllactose (2'-FL), 3-fucosyllactose (3-FL), 2',3-difucosyllactose (DiFL), and lacto-N-fucopentaose I (LNPFI).

12. The method of claim 5, wherein the aqueous solution is vacuum roller dried or vacuum drum dried at a shell temperature of about 80° C. to about 90° C.

13. The method of claim 6, wherein the aqueous solution is dried at a rotation speed of the drum cylinders of at least 1.0 rpm and less than 20 rpm.

14. The method of claim 7, wherein the aqueous solution is dried at a gap between the drum cylinders of at least 0.2 mm, and less than 10 mm.

15. The method of claim 1, wherein the aqueous solution has an ethanol content of at least 1.0% (v/v) and less than 50% (v/v).

16. The method of claim 1 wherein the aqueous solution comprising a purified human milk oligosaccharide has a total purity of at least 90% with respect to the weight of dry matter/solutes within the aqueous solution.

* * * * *